(12) United States Patent
Desai et al.

(10) Patent No.: US 10,722,882 B2
(45) Date of Patent: Jul. 28, 2020

(54) CHEMILUMINESCENT AND FLUORESCENT SUBSTRATE PADS AND USES THEREOF

(71) Applicant: PIERCE BIOTECHNOLOGY, INC., Carlsbad, CA (US)

(72) Inventors: Surbhi Desai, Rockford, IL (US); Kari Severson, Rockford, IL (US)

(73) Assignee: Pierce Biotechnology, Inc., Rockford, IL (US)

( * ) Notice: Subject to any disclaimer, the term of this patent is extended or adjusted under 35 U.S.C. 154(b) by 206 days.

(21) Appl. No.: 15/667,864

(22) Filed: Aug. 3, 2017

(65) Prior Publication Data

US 2018/0043355 A1 Feb. 15, 2018

Related U.S. Application Data

(60) Provisional application No. 62/370,542, filed on Aug. 3, 2016.

(51) Int. Cl.

| | |
|---|---|
| *B01L 3/00* | (2006.01) |
| *G01N 33/543* | (2006.01) |
| *G01N 33/58* | (2006.01) |
| *C12Q 1/28* | (2006.01) |
| *G01N 21/76* | (2006.01) |
| *G01N 33/533* | (2006.01) |
| *C09K 11/06* | (2006.01) |
| *F21K 2/06* | (2006.01) |
| *G01N 21/64* | (2006.01) |
| *G01N 21/77* | (2006.01) |

(52) U.S. Cl.
CPC ............ *B01L 3/5023* (2013.01); *C09K 11/06* (2013.01); *C12Q 1/28* (2013.01); *F21K 2/06* (2013.01); *G01N 21/6428* (2013.01); *G01N 21/76* (2013.01); *G01N 33/533* (2013.01); *G01N 33/54306* (2013.01); *G01N 33/54386* (2013.01); *G01N 33/54393* (2013.01); *G01N 33/581* (2013.01); *B01L 2200/16* (2013.01); *B01L 2300/069* (2013.01); *B01L 2300/12* (2013.01); *G01N 2021/7706* (2013.01)

(58) Field of Classification Search
CPC .......... B01L 2200/16; B01L 2300/069; B01L 2300/12; B01L 3/5023; C09K 11/06; C12Q 1/28; F21K 2/06; G01N 2021/7706; G01N 21/6428; G01N 21/76; G01N 33/533; G01N 33/54306; G01N 33/54386; G01N 33/54393; G01N 33/581

See application file for complete search history.

(56) References Cited

U.S. PATENT DOCUMENTS

| | | | |
|---|---|---|---|
| 5,089,424 A * | 2/1992 | Khalil | G01N 33/521 436/518 |
| 5,641,635 A | 6/1997 | Emmons et al. | |
| 9,709,527 B2 * | 7/2017 | Dworecki | G01N 27/44726 |
| 2001/0046681 A1 | 11/2001 | Senapathy | |
| 2002/0192736 A1 | 12/2002 | David et al. | |
| 2005/0068760 A1 | 3/2005 | Goychrach | |
| 2015/0083593 A1* | 3/2015 | Dworecki | G01N 27/44726 204/456 |
| 2017/0292932 A1* | 10/2017 | Dworecki | G01N 27/44726 |

FOREIGN PATENT DOCUMENTS

| | | |
|---|---|---|
| EP | 0254051 A2 | 1/1988 |
| EP | 0424634 | 5/1991 |

OTHER PUBLICATIONS

Liu et al., "A Novel Probe Au(III) for Chemiluminescent Image Detection of Protein Blots on Nitrocellulose Membranes," J. Proteome Res., 2008, vol. 7, No. 5, pp. 1884-1890.*

Printout retrieved from https://www.jensentools.com/acl-8099-lint-free-45-polyester-and-55-cellulose-wipes-9-x-9-100-bag/p/483-868 on Sep. 9, 2019.*

Carter, T. et al., "Investigation of a novel solid-phase chemiluminescent analytical system, incorporating photographic detection, for the measurement of glucose", *Talanta*, Elsevier, Amsterdam, NL, vol. 29, No. 6, 1982, pp. 1982, 529-531.

Harper, D. et al., "Nonuniform variation in band pattern with luminol/horseradish peroxidase Western blotting", *Analytical Biochemistry*, Elsevier, Amsterdam, NL, vol. 192, No. 1, 1991, pp. 59-63., 1991, 59-63.

* cited by examiner

*Primary Examiner* — Galina M. Yakovleva

(57) ABSTRACT

The disclosure provides compositions, kits and methods comprising an absorbent pad comprising a fibrous material and a liquid formulation comprising a luminescent substrate for identifying and quantifying biomolecule analytes.

17 Claims, 3 Drawing Sheets

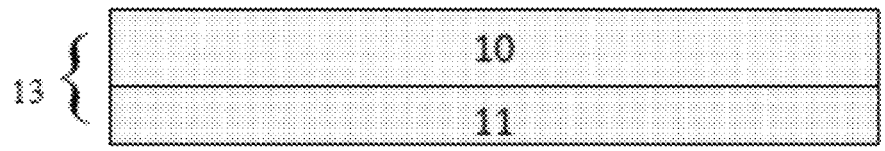
FIG. 1
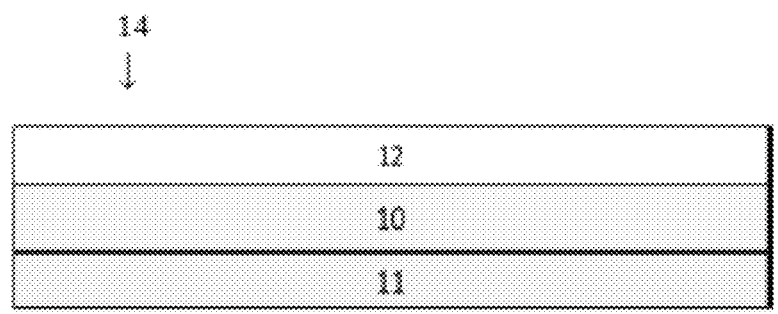
FIG. 2
FIG. 3

FIG. 4

CHEMILUMINESCENT AND FLUORESCENT SUBSTRATE PADS AND USES THEREOF

RELATED APPLICATION DATA

The present application is related to and claims the priority of U.S. Provisional Application No. 62/370,542 filed Aug. 3, 2016, the entire contents of which are incorporated herein by reference.

FIELD OF THE DISCLOSURE

The present disclosure is directed to compositions, kits, and methods for identifying and quantifying biomolecule analytes in blot assays.

BACKGROUND

Analytic detection of biomolecule analytes (e.g., proteins, nucleic acids, carbohydrates, lipids, etc.) is fundamental to molecular biology. In many applications, it is desirable to detect the presence of one or more particular molecules in a sample. For example, identification of a particular DNA sequence within a mixture of restriction fragments is used to determine the presence, position, and number of copies of a gene in a genome. It is also an integral technique in DNA typing. Analytic detection is also used, e.g., in disease diagnosis and drug development, to determine the presence of a particular antibody or protein, e.g., in a blood sample or large chemical library. Detection of biomolecule analytes is therefore of fundamental value in diagnostic medicine. To meet these needs, many techniques, e.g., DNA blotting, RNA blotting, protein blotting, and immune assays such as but not limited to, ELISA assays, have been developed to detect the presence of a particular molecules or fragment in the midst of a complex sample containing similar molecules.

Western blotting is one tool to identify and quantify a specific protein in a complex mixture. This technique enables indirect detection of protein samples immobilized on a membrane, such as a nitrocellulose membrane, a nylon membrane, or a polyvinylidene fluoride membrane. In a conventional Western blot, protein samples are first resolved by SDS-PAGE and then electrophoretically transferred to the membrane. Following a blocking step, the membrane is probed with a primary antibody (poly- or monoclonal) that was raised against the antigen to be detected. After a subsequent washing step, the membrane is incubated with an enzyme-conjugated secondary antibody that is reactive toward the primary antibody. The activity of the enzyme, such as alkaline phosphatase or horseradish peroxidase, is necessary for signal generation, when the secondary antibody interacts with the primary antibody. Finally, the membrane is washed again, and incubated with an appropriate enzyme substrate (e.g., a chemiluminescent substrate) to produce a recordable signal.

Western blotting substrates are often luminol-based and produce a chemiluminescent signal. Chemiluminescence is a chemical reaction that produces energy released in the form of light. In the presence of horseradish perioxidase, luminol forms an excited state product that emits light as it decays to the ground state. Light emission occurs only during the enzyme-substrate reaction and, therefore, once the substrate in proximity to the enzyme is exhausted, signal output ends.

Because a Western blot is composed of a series of linked techniques that require skill to perform, failure to capture a signal can be caused by many factors. For example, the final step for obtaining the chemiluminescent signal may be time-consuming and subject to human error. This final step typically requires (1) preparing the chemiluminescent substrate solution (e.g., combining a luminol substrate solution with a stable peroxide buffer), (2) placing the antibody conjugate-probed membrane in the substrate solution, (3) incubating the antibody conjugate-probed membrane in the substrate solution (e.g., for at least 5 minutes), (4) preparing a blot membrane or sheet protector, (5) placing the incubated membrane in the blot membrane or sheet protector, and (6) transferring the incubated membrane to an image capturing device. There is a need in the art to replace this process with more efficient and accurate processes. The present disclosure is directed to solving this and other needs in the art.

SUMMARY

The present disclosure provides, inter alia, a composition comprising an absorbent pad comprising a fibrous material and a liquid formulation, wherein the liquid formulation comprises a luminescent substrate. In some embodiments, the luminescent substrate is a chemiluminescent substrate. In some embodiments, the luminescent substrate is a fluorescent substrate.

In some embodiments, an absorbent pad of the disclosure has a thickness from about 0.2 mm to about 3 mm; and/or has an extrinsic absorbency from about 150 mL/$m^2$ to about 500 mL/$m^2$; and is impregnated with a liquid formulation comprising a luminescent substrate, the aforementioned ranges comprising any intermediate numbers inbetween.

In some embodiments, an absorbent pad of the disclosure further comprises: a basis weight from about 25 g/$m^2$ to about 100 g/$m^2$ or a basis weight from about 50 g/$m^2$ to about 70 g/$m^2$, the aforementioned ranges comprising any intermediate numbers inbetween.

In some embodiments, an absorbent pad of the disclosure comprises: (i) a thickness of from about 0.2 mm to about 1 mm; and (ii) an extrinsic absorbency of from about 250 mL/$m^2$ to about 400 mL/$m^2$.

In some embodiments, an absorbent pad of the disclosure comprises: (i) a thickness of from about 0.3 mm to about 0.7 mm; and (ii) an extrinsic absorbency of from about 250 mL/$m^2$ to about 400 mL/$m^2$.

In some embodiments, an absorbent pad of the disclosure comprises: (1) a fibrous material and (2) a liquid formulation which comprises a luminescent substrate; wherein the pad: (i) has a thickness from about 0.2 mm to about 3 mm; (ii) has an extrinsic absorbency from about 150 mL/$m^2$ to about 500 mL/$m^2$; and (iii) is impregnated with the liquid formulation.

In some embodiments, an absorbent pad of the disclosure: (i) has a thickness from about 0.2 mm to about 1 mm; (ii) has an extrinsic absorbency from about 250 mL/$m^2$ to about 400 mL/$m^2$; and (iii) has a basis weight from about 25 g/$m^2$ to about 100 g/$m^2$.

In some embodiments, an absorbent pad of the disclosure: (i) has a thickness from about 0.3 mm to about 0.7 mm; (ii) has an extrinsic absorbency from about 250 mL/$m^2$ to about 400 mL/$m^2$; and (iii) has a basis weight from about 50 g/$m^2$ to about 70 g/$m^2$.

Exemplary fibrous material that an absorbent pad of the disclosure can comprise include: a natural fiber, a synthetic fiber, or a combination thereof. In some embodiments, fibrous material of an absorbent pad of the disclosure comprises: a polyester, a cellulose polymer, or a polyester/cellulose polymer blend. In some embodiments, fibrous material of an absorbent pad of the disclosure comprises: a hydroentangled polyester/cellulose blend.

In some embodiments, a polyester/cellulose polymer blend comprises about 40 wt % to about 50 wt % polyester and about 50 wt % to about 60 wt % cellulose. In some embodiments, a polyester/cellulose polymer blend comprises about 45 wt % polyester and about 55 wt % cellulose.

In some embodiments, fibrous material of an absorbent pad of the disclosure comprises a polyester, a cellulose polymer, a polyamide, cotton, fleece, felt, a glass fiber, a filter paper, a soft wood filter, nylon, or a combination of one or more thereof. In some embodiments, fibrous material of an absorbent pad of the disclosure comprises a polyester, a cellulose polymer, a polyamide, cotton, fleece, felt, a glass fiber, a filter paper, a soft wood filter, nylon, a combination of one or more thereof or a combination of two or more thereof.

In some embodiments, a pad of the disclosure is non-woven. In some embodiments, a pad of the disclosure is woven.

In some embodiments, a pad of the disclosure is a single layered pad. In some embodiments, a pad of the disclosure is has 1 to 10 layers (including any numbers between 1 and 10). In some embodiments, a pad of the disclosure is has 1 layer, 2 layers, or 3 layers. In some embodiments, an absorbent pad of the disclosure has one layer, two layers, three layers, four layers, five layers, six layers, seven layers, eight layers, nine layers or ten layers.

Several luminescent substrates of a variety of enzymes can be used in a pad of the disclosure. Some example luminescent substrates include, but are not limited to, a substrate of horseradish peroxidase, a substrate of alkaline phosphatase, a substrate of β-galactosidase, a substrate of β-glucosidase, a substrate of β-glucuronidase, a substrate of arylesterase, a substrate of sulfatase, or a combination of one or more substrates thereof or a combination of two or more substrates thereof.

In some embodiments, a luminescent substrate used in a pad of the disclosure is a chemiluminescent substrate. In some exemplary embodiments, a chemiluminescent substrate used in a pad of the disclosure is an acridane compound or a 1,2-dioxetane. An exemplary chemiluminescent substrate used in a pad of the disclosure is:

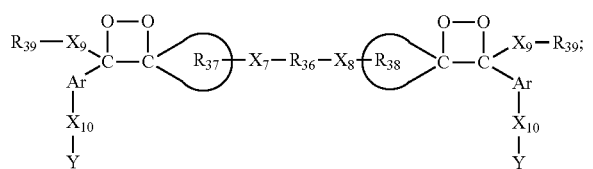

wherein each of $R_{36}$ and $R_{39}$ is an alkyl group; $R_{37}$ and $R_{38}$ are each an adamantly spirofused to the carbon atom of the dioxetane ring; Ar is a substituted phenyl which may optionally include a deuterium atom or a deuterium atom containing organic group; $X_7$, $X_8$, $X_9$, and $X_{10}$ are each oxygen; and Y is a diphosphonium group.

In some exemplary embodiments, a chemiluminescent substrate used in a pad of the disclosure is phenyl 10-methyl($D_3$)acridan-9-carboxylate; phenyl($D_5$) 10-methyl($D_3$)acridan-9-carboxylate; 2,2,2-trifluoroethyl 10-methyl($D_3$)acridan-9-carboxylate; phenyl($D_5$)10-methylacridan-9-carboxylate; 4,4'-biphenyl 10-methylacridan-9-carboxylate; [(4-methoxy($D_3$))-4-(3-hydroxy-4-chlorophenyl)]spiro[1,2-dioxetane-3,2'-adamantane]-10-methylacridan-9-carboxylate; [(4-methoxy($D_3$)-4-(3-hydroxy-4-chlorophenyl)]spiro[1,2-dioxetane-3,13-tricyclo[7.3.1.0$^{2,7}$]tridec-2,7-ene]-10-methyl($D_3$)acridan-9-carboxylate; 4'-carboxylic acid-4-biphenyl 10-methylacridan-9-carboxylate; [4-(2-propenoic acid)]phenyl-10-methyl-9-carboxylate; bis-(1,2-ethane)10-methylacridan-9-carboxylate; bis-(1,4-phenoxy)10 methylacridan-9-carboxylate; bis-(1,5-naphthyl) 10-methylacridan-9-carboxylate; [(4-phenoxy)-4-(3-phosphoryloxy-4-chlorophenyl)]spiro[1,2-dioxetane-3,13'-tricyclo[7.3.1.0$^{2,7}$]tridec-2,7-ene; [4-(4-chlorophenoxy)-4-(3-phosphoryloxy-4-chlorophenyl)]spiro[1,2-dioxetane-3,13'-tricyclo[7.3.1.0$^{2,7}$]tridec-2,7-ene; [4-(2,4,6-trichlorophenoxy)-4-(3-phosphoryloxy-4-chlorophenyl)]spiro[1,2-dioxetane-3,13'-tricyclo[7.3.1.0$^{2,7}$]tridec-2,7-ene; [4-methoxy-4-(3-phosphoryloxy-4-cyanophenyl)]spiro[1,2 dioxetane-3,13'-tricycle[7.3.1.0$^{2,7}$]tridec-2,7-ene; [(4-methoxy($D_3$)-4-(3-phosphoryloxy-4-cyanophenyl)]spiro[1,2-dioxetane-3,2'-5-chloroadamantane]; [(4-methoxy($D_3$)-4-(3-phosphoryloxy-4-cyanophenyl)]spiro[1,2-dioxetane-3,2'-5-methoxyadamantane]; [(4-methoxy($D_3$)-4-(3-phosphoryloxy-4-cyanophenyl)]spiro[1,2-dioxetane-3,13'-tricycle[7.3.1.0$^{2,7}$]tridec-2,7-ene; bis {[(4-methylenoxy)-4-(3-phosphoryloxyphenyl)]spiro[1,2-dioxetane-3,2'-adamantane]; bis-{[(4-methylenoxy)-4-(3-phosphoryloxy-4-cholorophenyl)]spiro[1,2-dioxetane-3,2'-adamantane]; bis-[(4-methoxy)-4-(3-phosphoryloxy-4-cholorophenyl)] spiro[1,2-dioxetane-3,2'-5-chloroadamantane]; bis{[(4-methoxy)-4-(3-phosphoryloxy-4-chlorophenyl)]spiro[1,2-dioxetane-3,13'-tricyclo[7.3.1.0$^{2,7}$]tridec-2,7-ene]; bis{(4-methoxy($D_3$)-4-(3-phosphoryloxy-4-chlorophenyl)}spiro{1,2-dioxetane-3,2'-(5-oxy-adamantane)}methane; bis{(4-methoxy($D_3$)-4-(3-phosphoryloxy-4-cyanophenyl)}spiro {1,2-dioxetane-3,2'-(5-oxy-adamantane)}methane; bis{(4-methoxy-4-(3-phosphoryloxyphenyl)}spiro {1,2-dioxetane-3,2'-(5-oxy-adamantane)}methane; [4-methoxy ($D_3$)-4-(3-β-D-galactose-4-chlorophenyl)]spiro[1,2-dioxetane-3,2'-adamantane]; [(4-methoxy-4(3-β-D-galactose-4-cyanophenyl)]spiro[1,2-dioxetane-3-1,3-tricylo[7.3.1.0$^{2,7}$] tridec-2,7-ene; [(4-methoxy($D_3$)-4-(3-β-D-glucoside-4-chlorophenyl)]spiro[1,2-dioxetane-3,2'-adamantane]; [(4-methoxy-4(3-β-D-glucoside-4-cyanophenyl)]spiro[1,2-dioxetane-3-1,3-tricylo[7.3.1.0$^{2,7}$]tridec-2,7-ene; [(4-methoxy($D_3$)-4-(3-3-D-glucoronic acid-4-chlorophenyl)] spiro[1,2-dioxetane-3,2'-adamantane]; [(4-methoxy-4(3-β-D-glucoronic acid-4-cyanophenyl)]spiro[1,2-dioxetane-3-1, 3-tricylo[7.3.1.0$^{2,7}$]tridec-2,7-ene; [(4-methoxy($D_3$)-4-(3-acetoxy-4-chlorophenyl)]spiro[1,2-dioxetane-3,2'-adamantane]; [(4-methoxy-4(3-acetoxy-4-cyanophenyl)]spiro[1,2-dioxetane-3-1,3-tricylo[7.3.1.0$^{2,7}$]tridec-2,7-ene; [(4-methoxy($D_3$)-4-(3-sulfate-4-chlorophenyl)]spiro[1,2-dioxetane-3,2'-adamantane]; [(4-methoxy-4(3-sulfate-4-cyanophenyl)]spiro[1,2-dioxetane-3-1,3-tricylo[7.3.1.0$^{2,7}$]tridec-2,7-ene; a salt of one of the foregoing; or a mixture of one or more thereof; or a mixture of two or more thereof.

In some exemplary embodiments, a chemiluminescent substrate used in a pad of the disclosure, is resorcinol, pyrogallol, phloroglucinol, purpurogallin, aminoaryl cyclic diacylhydrazide or a salt thereof, hydroxyaryl cyclic diacylhydrazide, a pyridopyridazine derivative, 10,10'-dimethyl-9,9-biacridane, 9-benzylidene-10-methylacridane, a substituted-9-benzylidene-10-methylacridane, N-methylacridane, a substituted N-methylacridane, 9-benzylacridane, a substituted-9-benzylacridane, 9-benzyl-N-methylacridane, a substituted-9-benzyl-N-methylacridane, N-alkylacridane-9-carboxylic acid, an ester of N-alkylacridane-9-carboxylic acid, a thioester of N-alkylacridane-9-carboxylic acid, indole-3-acetic acid, an ester of indole-3-acetic acid, a thioester of indole-3-acetic acid, N-methylindole-3-acetic acid, an ester of N-methylindole-3-acetic acid, phenyl, phenyl-2-(6'-hydroxy-2-benzothiazolyl-A$^2$-thiazoline-4-carboxylate, substituted phenyl-2-(6'-hydroxy-2-benzothiazolyl-A$^2$-thiazoline-4-carboxylate, methyl 2-(6'-hydroxy-2'-benzothiazolyl)-A$^2$-thiazoline-4-carboxylate, 2-(6'- hydroxy-2'-benzothiazolyl)-$\Delta^2$-thiazoline acetic acid, an ester of 2-(6'-hydroxy-2'-benzothiazolyl)-$\Delta^2$-thiazoline acetic acid, 2-(4'-hydroxyphenyl)thiazole-4-carboxylic acid hydrazide, 2-(6'-hydroxy-2'-benzothiazolyl)thiazole-4-carboxylic acid hydrazide, substituted or unsubstituted 9-acridanecarboxylic acid hydrazide, substituted or unsubstituted N-alkyl-9-acridanecarboxylic acid hydrazide, substituted N-alkyl-9-30 acridanecarboxylic acid hydrazide, o-hydroxybenzoic acid hydrazide, o-aminobenzoic acid hydrazide, m-hydroxybenzoic acid hydrazide, 2-hydroxy-3-naphthoic acid hydrazide, 2-amino-3-naphthoic acid hydrazide, 1-hydroxy-2-anthroic acid hydrazide, D-luciferin-O-sulphate, D-luciferin-O-phosphate, a luciferin isolated from *Pholas dactlus*, the firefly *Photinus Pyralis* or Cypridina, and mixtures thereof; and wherein when the compound is an aryl compound, then the aryl component is phenyl, substituted phenyl, naphthyl, substituted naphthyl, anthxyl or substituted anthryl.

In some exemplary embodiments, a chemiluminescent substrate used in a pad of the disclosure is luminol, isoluminol, acridane, phenyl-10-methylacridane-9-carboxylate, 2,4,6-trichiorophenyl-10-methylacndane-9-carboxylate, pyrogallol, phloroglucinol, resorcinol, or a combination of one or more thereof, or a combination of two or more thereof. In some exemplary embodiments, a chemiluminescent substrate used in a pad of the disclosure is luminol, or isoluminol.

In some exemplary embodiments, a luminescent substrate used in a pad of the disclosure is a fluorescent substrate. In some exemplary embodiments, a fluorescent substrate used in a pad of the disclosure is 3-(4-hydroxyphenyl)propionic acid.

In some embodiments, a liquid formulation comprising an absorbent pad of the disclosure further comprises one or more of an oxidizing agent, a buffer, a stabilizing agent, an enhancer, or a combination of one or more thereof. In some embodiments, a liquid formulation comprising an absorbent pad of the disclosure further comprises one or more of an oxidizing agent, a buffer, a stabilizing agent, an enhancer, or a combination of one or more thereof, or a combination of two or more thereof In some embodiments, a liquid formulation comprising an absorbent pad of the disclosure further comprises an oxidizing agent. Exemplary oxidizing agents include but are not limited to a peroxide compound or a compound that produces a peroxide in situ. Additional exemplary oxidizing agents include, but are not limited to, hydrogen peroxide, urea hydrogen peroxide, sodium carbonate hydrogen peroxide, a perborate salt, or a combination of one or more thereof, or a combination of two or more thereof.

In some embodiments, a liquid formulation comprising an absorbent pad of the disclosure further comprises a stabilizing agent. Exemplary stabilizing agents include, but are not limited to, a cyclodextrin, a dextrin, a sulfate, a sugar, a nonionic surfactant, an anionic surfactant, an ethylene oxide/propylene oxide adduct, or a combination of or a combination of one or more thereof, or a combination of two or more thereof. Additional, exemplary stabilizing agent include, but are not limited to, polyoxyethylenesorbitan monolaurate, polyoxyethylenesorbitan monopalmitate, polyethylene glycol sorbitan monostearate, polyethylene glycol sorbitan monooleate, polyoxyethylenesorbitan trioleate, t-octylphenoxypolyethoxyethanol, polyethylene glycol nonylphenyl ether, polyethylene glycol tert-octylphenyl ether, polyethylene glycol tert-octylphenyl ether, polyethylene glycol dodecyl ether, or a combination of one or more thereof, or a combination of two or more thereof.

In some embodiments, a liquid formulation comprising an absorbent pad of the disclosure further comprises a buffer. Exemplary buffers include, but are not limited to, ethylenediamine tetraacetic acid, succinate, citrate, aspartic acid, glutamic acid, maleate, cacodylate, 2-(N-morpholino)-ethanesulfonic acid, N-(2-acetamido)-2-aminoethanesulfonic acid, piperazine-N,N'-2-ethanesulfonic acid, 2-(N-morpholino)-2-hydroxy-propanesulfonic acid, N,N-bis-(hydroxyethyl)-2-aminoethanesulfonic acid, 3-(N-morpholino)-propanesulfonic acid, N-2-hydroxyethyl-piperazine-N-2-ethanesulfonic acid, 3-(N-tris-(hydroxymethyl)methylamino)-2-hydroxypropanesulfonic acid, 3-(N,N-bis[2-hydroxyethyl]amino)-2-hydroxypropanesulfonic acid, N-(2-hydroxyethyl)piperazine-N'-(2-hydroxypropanesulfonic acid), 4-(2-hydroxyethyl)-1-piperazine propanesulfonic acid, N-[tris(hydroxymethyl)-methyl]glycine, N,N-bis(2-hydroxyethyl)glycine, (2-hydroxy-1,1-bis(hydroxymethyl)ethyl)amino]-1-propanesulfonic acid, N-(1,1-dimethyl-2-hydroxyethyl)-3-amino-2-hydroxypropanesulfonic acid, tris(hydroxy methyl)amino-methane, and bis[2-hydroxyethyl]iminotris-[hydroxymethyl]methane, or a combination of one or more thereof, or a combination of two or more thereof.

In some embodiments, a liquid formulation comprising an absorbent pad of the disclosure further comprises an enhancer. Exemplary enhancers include, but are not limited to, a halogenated phenols; an alkylated phenol; 4-benzylphenol; 4-(2',4'-dinitrostyryl) phenol; 2,4-dichlorophenol; p-hydroxycinnamic acid; p-fluorocinnamic acid; p-nitroicinnamic acid; p-aminocinnamic acid; m-hydroxycinnamic acid; o-hydroxycinnamic acid; 4-phenoxyphenol; 4-(4-hydroxyphenoxy) phenol; p-phenylphenol; 2-chloro-4-phenylphenol; 4'-(4'-hydroxyphenyl) benzophenone; 4-(phenylazo) phenol; 4-(2'-carboxyphenylaza) phenol; 1,6-dibromonaphtho-2-ol; 1-bromonaphtho-2-ol; 2-naphthol; 6-bromonaphth-2-ol; 6-hydroxybenzothiazole; 2-amino-6-hydroxybenzothiazole; 2,6-dihydroxybenzothiazole; 2-cyano-6-hydroxybenzothiazole; dehydroluciferin; firefly luciferin; phenolindophenol; 2,6-dichlorophenolindophenol; 2,6-dichlorophenol-o-cresol; phenolindoaniline; a substituted or unsubstituted N-alkylphenoxazine; a substituted or unsubstituted N-alkylphenothiazine; a substituted or unsubstituted N-alkylpyrimidylphenoxazine; N-alkylpyridylphenoxazine; a substituted or unsubstituted 2-hydroxy-9-fluorenone; a substituted or unsubstituted 6-hydroxybenzoxazole, or a combination of one or more thereof, or a combination of two or more thereof.

In some embodiments, a liquid formulation comprising an absorbent pad of the disclosure further comprises is an aqueous formulation.

In some embodiments, a composition of the disclosure comprises an absorbent pad as described in embodiments above, further comprising a blot membrane in fluid contact with the pad, wherein the blot membrane comprises a biomolecule analyte bound to a detection agent, and the detection agent is reactive with a luminescent substrate, such as one or more luminescent substrates described above, including chemiluminescent substrates or fluorescent substrates.

In some embodiments, a biomolecule analyte is a protein, a nucleic acid, a lipid or a carbohydrate. The blot membrane can be a Northern blot membrane, a Western blot membrane, or a Southern blot membrane.

In some embodiments, an exemplary detection agent comprises an enzyme reactive with the chemiluminescent substrate. In some embodiments, a detection agent comprises an antibody or a fragment thereof. Exemplary detection agents include a primary antibody or a fragment thereof bound directly to or capable of binding to a biomolecule analyte; a secondary antibody or a fragment thereof bound to or capable of binding to a primary antibody or a fragment thereof. In some embodiments, the secondary antibody or fragment thereof is attached to an enzyme or is associated with an enzyme or comprises an enzyme and is reactive with the substrate in the absorbent pad.

In some embodiments, the enzyme is horseradish peroxidase, alkaline phosphatase, β-galactosidase, β-glucosidase, β-glucuronidase, arylesterase, sulfatase, or a combination of one or more thereof, or a combination of two or more thereof.

In some embodiments, in an absorbent pad of the disclosure, a biomolecule analyte is a protein and the enzyme is horseradish peroxidase, alkaline phosphatase, 3-galactosidase, 3-glucosidase, (3-glucuronidase, arylesterase, sulfatase, or a combination of one or more thereof, or a combination of two or more thereof.

In some embodiments, in an absorbent pad of the disclosure, a biomolecule analyte is a protein and an enzyme is horseradish peroxidase. In some embodiments, a detection agent comprises biotin and streptavidin.

The present disclosure also provides kits containing one or more absorbent pads. Kits according to the disclosure provide short term and long term storage of the absorbent pads with minimal to no degradation of the luminescent substrate in the absorbent pad. The absorbent pads can optionally be individually wrapped or packaged within the kit.

A kit of the present disclosure, in various embodiments, comprises one or more of the various absorbent pads as described in embodiments infra and supra wherein an absorbent pad contains a fibrous material and a liquid formulation, and wherein the liquid formulation contains a luminescent substrate. A kit of the disclosure can comprise absorbent pads having a fibrous material, and a liquid formulation comprising a chemiluminescent substrate or a fluorescent substrate, including any of the exemplary fibrous materials and substrates as set forth in other sections herein.

In some embodiments, a kit of the disclosure comprising one or more absorbent pads of the disclosure, can comprise a liquid formulation further comprising one or more reagents including: an oxidizing agent, a buffer, a stabilizing agent, an enhancer, or a combination of one or more thereof or a combination of two or more thereof.

In some embodiments, a kit of the disclosure, can further comprise a detection agent, packaged in separate container or packaging from the absorbent pads. In some embodiments, a detection agent of a kit of the disclosure comprises an antibody or a fragment thereof. Exemplary detection agents include a primary antibody or a fragment thereof bound directly to or capable of binding to a biomolecule analyte; a secondary antibody or a fragment thereof bound to or capable of binding to a primary antibody or a fragment thereof. In some embodiments, the secondary antibody or fragment thereof is attached to an enzyme or comprises an enzyme and is reactive with the substrate in the absorbent pad.

In some embodiments, the enzyme is horseradish peroxidase, alkaline phosphatase, β-galactosidase, β-glucosidase, β-glucuronidase, arylesterase, sulfatase, or a combination of one or more thereof or a combination of two or more thereof.

In some embodiments, a detection agent of the kit comprises biotin and streptavidin.

A kit of the disclosure provides storage stability for the pads for a time period of from about 3 months to about 3 years, including any time in between. In some embodiments a kit of the disclosure comprises at least two pads that are separately sealed.

The disclosure additionally provides compositions comprising an absorbent pad of the disclosure in fluid contact with a blot membrane; where the absorbent pad contains a fibrous material and a liquid formulation which contains a luminescent substrate; and wherein the blot membrane includes a biomolecule analyte bound to a detection agent, and the detection agent is reactive with a luminescent substrate. In some embodiments, the pad has a thickness from about 0.2 mm to about 3 mm; and/or has an extrinsic absorbency from about 150 mL/m$^2$ to about 500 mL/m$^2$; and is impregnated with the liquid formulation.

In some embodiments, the disclosure provides a device system comprising an absorbent pad as described herein supra and infra and a chemiluminescent imaging device. In some embodiments, a chemiluminescent imaging device comprises a charge-coupled device camera.

The disclosure additionally provides methods for detecting biomolecule analytes in biological samples by the steps of: (a) separating biomolecular components of a biological sample using gel electrophoresis thereby forming a separation gel comprising separated biomolecular components, wherein the separated biomolecular components comprise a biomolecule analyte; (b) transferring the separated biomolecular components to a blot membrane; (c) contacting the blot membrane with a detection agent and allowing the detection agent to bind to the biological analyte, wherein the detection agent is reactive with a luminescent substrate; (d) contacting the blot membrane with an absorbent pad according to the present disclosure, to react the luminescent substrate with the detection agent thereby forming a luminescent signal; and (e) detecting the luminescent signal thereby detecting the biomolecule analyte. An absorbent pad according to the present disclosure contains a fibrous material and a liquid formulation which comprises a luminescent substrate. In various embodiments of a method of the disclosure, the blot membrane can be a Western blot membrane, a Northern blot membrane, or a Southern blot membrane.

In some embodiments, the disclosure provides method for detecting a biomolecule analyte in a biological sample comprising: (a) placing an absorbent pad as described herein supra and infra in a luminescent imaging device; and (b) detecting light emitted from the luminescent reaction in the pad thereby detecting the biomolecule analyte.

In some embodiments of a method of the disclosure, the imaging device is a chemiluminescent imaging device, and the reaction is a chemiluminescent reaction. In some embodiments, the imaging device is a fluorescent imaging device, and the reaction is a fluorescent reaction.

In some embodiments of a method of the disclosure, the biomolecule analyte is a protein and the enzyme is horseradish peroxidase, alkaline phosphatase, (3-galactosidase, 3-glucosidase, (3-glucuronidase, arylesterase, sulfatase, or a combination of two or more thereof.

In some embodiments of a method of the disclosure, contacting the blot membrane with an absorbent pad comprises applying pressure to the blot membrane, the pad, or both. In some embodiments of a method of the disclosure, contacting the blot membrane with an absorbent pad comprises applying a roller against the surface of the blot membrane or the pad to create a full, flat surface contact between the blot membrane and the pad.

In some embodiments of a method of the disclosure, detecting the luminescent signal or imaging a luminescent signal occurs over a period of from about 1 minute to about 2 hours, including times in between such as but not limited to 1 minute, 5 minutes, 10 minutes, 15, minutes, 20 minutes, 25 minutes, 30 minutes, 40 minutes, 50 minutes, 60 minutes, 70 minutes, 80 minutes, 90 minutes, 100 minutes, 120 minutes.

These and other aspects of the disclosure are described herein.

BRIEF DESCRIPTION OF THE DRAWINGS

FIG. 1 depicts an absorbent pad (11) is in fluid contact with a blot membrane (10). The absorbent pad (11) and blot membrane (10) form a layered matrix (13). The layered matrix (13) allows for the movement of the liquid formulation from the absorbent pad (11) into the blot membrane (10) to provide for the luminescent (e.g., chemiluminescent) reaction between the enzyme and the chemiluminescent substrate.

FIG. 2 depicts a protective sheet (12) on top of a blot membrane (10) which is in fluid contact with an absorbent pad (11), thus forming a second layered matrix (14). The protective sheet (12) is useful when using a roller to apply pressure to the protective sheet (10) in order to provide for substantially complete fluid contact between the blot membrane (10) and the absorbent pad (11) to allow the liquid formulation in the absorbent pad (11) to soak the blot membrane (10) and initiate the luminescent (e.g., chemiluminescent) reaction. Using a roller or providing pressure by an alternative means can be used to remove any air bubbles.

FIG. 3 provides the results from a Western blot assay obtained from a charge-coupled device (CCD) imager over the course of one hour using the materials and methods described herein. "No pad" represents existing methods in the art that use liquid substrates, and "Absorbent Pad 1" and "Absorbent Pad 2" represent exemplary embodiments of the present disclosure.

FIG. 4 provides the results from a Western blot assay obtained from a CCD imager over the course of one hour using the materials and methods described herein. "No pad" represents existing methods in the art that use liquid substrates, and "Absorbent Pad 1" and "Absorbent Pad 2" represent exemplary composition embodiments of the present disclosure.

DETAILED DESCRIPTION

Definitions

Figure 5:
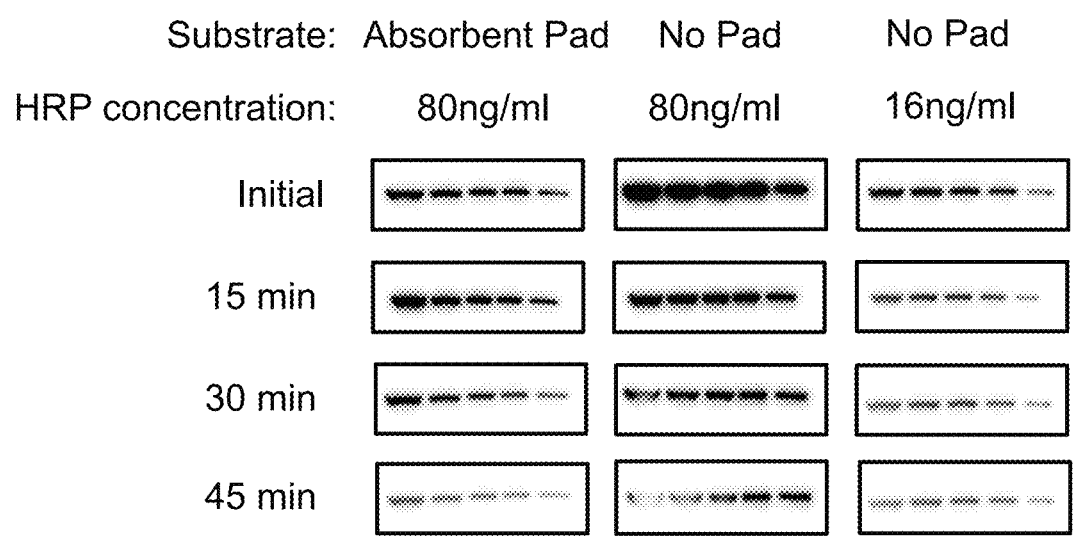
FIG. 5 provides the results from a Western blot assay obtained from a CCD imager over the course of one hour using the materials and methods described herein. "No pad" represents existing methods in the art that use liquid substrates, while "Absorbent Pad 1" and "Absorbent Pad 2" represent exemplary composition embodiments of the present disclosure.

"Pad" refers to a fibrous material. A pad can be a woven or a nonwoven fibrous material, and can contain natural fibers, synthetic fibers, or a combination thereof.

"Absorbent" refers to a fibrous material that can soak up or absorb a liquid formulation, and that can typically substantially retain or hold the liquid formulation within the material. "Absorbent" fibrous materials are typically porous, permeable, and/or pervious.

"Luminescent substrate" refers to a substrate that can produce photons of light. Luminescence is the emission of light from a substance as it goes from a ground state to an electronically excited state. A luminescent substrate can be a chemiluminescent substrate, a fluorescent substrate, a bioluminescent substrate, or the like. A chemiluminescent substrate produces light as a result of a chemical reaction, for example between the substrate and an enzyme. A fluorescent substrate produces light when it is electronically excited by a particular wavelength of light.

"Liquid formulation" refers to a composition within a liquid medium, (e.g. in the form of a solution, suspension, or emulsion). A liquid formulation can be an aqueous formulation, an organic solvent formulation, or an oil formulation. In some embodiments, a liquid formulation is an aqueous solution. The liquid formulations herein include a luminescent substrate and, optionally, one or more compounds useful in producing or enhancing luminescent reactions and detection thereof. In some embodiments, the liquid formulations herein include a chemiluminescent substrate and one or more compounds useful in producing or enhancing the chemiluminescent reaction and/or detection of the chemiluminescent reaction. In some embodiments, the liquid formulations herein include a fluorescent substrate and one or more compounds useful in producing or enhancing the fluorescent reaction and/or detection of the fluorescent reaction.

"Impregnated" refers to a fibrous material containing a liquid formulation. The fibrous material may, for example, be soaked, saturated, or moistened with the liquid formulation. In some embodiments, a liquid formulation can be substantially evenly distributed throughout the fibrous material. Thus, a fibrous material that absorbs a liquid formulation may be "impregnated" with the liquid formulation and, therefore, may be an absorbent fibrous material. "Impregnated" fibrous materials may be infused, soaked, permeated, saturated, and/or moistened be with the liquid formulation.

"Blot" refers to a blot assay. Exemplary blot assays include Western blot, Southern blot, Northern blot, Far-Western blot, Southwestern blot, dot blot, and the like. In some embodiments, the "blot" is a Western blot, a dot blot, a Southern blot, or a Northern blot. In some embodiments, the "blot" is a Western blot.

"Blot membrane" refers to a membrane used when performing a blot assay in which separated biomolecular molecular components within a separation gel are transferred to the blot membrane. The separated biomolecular components may include, for example, one or more detection agents and one or more biomolecule analytes (e.g., proteins, nucleic acids, carbohydrates, lipids etc.). Depending on the stage of processing (e.g., in a Western blot assay), the membrane can further comprise primary antibodies and optionally secondary antibodies. A blot membrane is produced as follows: (a) separating biomolecular components of a biological sample using gel electrophoresis thereby forming a separation gel comprising separated biomolecular components, wherein the separated biomolecular components include a biomolecule analyte; (b) transferring the separated biomolecular components to a blot membrane; and (c) contacting the blot membrane with a detection agent and allowing the detection agent to bind to the biological analyte, wherein the detection agent is capable of reacting with a luminescent substrate. A blot membrane may be made of a material known in the art of blot assays, such as nitrocellulose or polyvinylidene fluoride, and may be purchased from a commercial supplier, such as Thermo Fisher Scientific (e.g., iBlot® Transfer Stack; nitrocellulose membrane).

"Biomolecule analyte" refers to a biological compound such as proteins, nucleic acids, fats, metabolites, or carbohydrate that is the subject of analysis (e.g. a blot assay). A biomolecule analyte is the biological compound that the skilled artisan is interested in identifying and/or quantifying. In some embodiments, the biomolecule analyte is a protein. In some embodiments, the biomolecule analyte is a nucleic acid. In some embodiments, the biomolecule analyte is a DNA sequence. In one embodiment, the biomolecule analyte is RNA or mRNA.

"Biological sample" refers to a biological material derived from a biological cell or an organism. Exemplary biological materials include blood, plasma, cells, tissue, chemical libraries, and the like.

"Biomolecular components" refer to materials present in a biological sample, such as proteins, fats, carbohydrates, metabolites and the like. The biomolecular components include the "biomolecule analyte" that is the target of interest and that is separated from the other biomolecular components in the blot assay.

"Detection agent" refers to a compound that is capable of interacting with (covalently or non-covalently) the biomolecule analyte and that can be identified and/or quantified, for example with a luminescent substrate. In some embodiments, the "detection agent" contains (1) a compound that is capable of interacting with (e.g. binding) the biomolecule analyte and (2) a label that can be identified and/or quantified with a luminescent substrate (also referred to herein as a detectable label), wherein the label is bound to the compound covalently or non-covalently. Exemplary compounds that can interact with a biomolecule analyte include antibodies (monoclonal or polyclonal), RNA, DNA, biotin, and the like. In one embodiment, the compound that interacts with the biomolecule analyte is, or includes, an antibody. The label can be any appropriate detectable label known in the art, such as an enzyme, streptavidin, avidin, or a combination thereof. In some embodiments, the label is horseradish peroxidase, alkaline phosphatase, β-galactosidase, β-glucosidase, β-glucuronidase, arylesterase, sulfatase, and the like. In some embodiments, the label is horseradish peroxidase or alkaline phosphatase. In some embodiments, the label is horseradish peroxidase. In some embodiments, the detection agent comprises an antibody bound to an enzyme. In some embodiments, the detection agent includes a primary antibody bound to a secondary antibody that is bound to an enzyme. In some embodiments, the biomolecule analyte is a protein, and the detection agent comprises a primary antibody bound to a secondary antibody that is bound to an enzyme. In some embodiments, the biomolecule analyte is a protein, and the detection agent comprises a primary antibody bound to a secondary antibody that is bound to horseradish peroxidase. In some embodiments, the detection agent comprises biotin and streptavidin. In some embodiments, the detection agent comprises biotin, streptavidin, and an enzyme. In some embodiments, the detection agent comprises biotin and avidin. In some embodiments, the detection agent comprises biotin, avidin, and an enzyme. The term "detection agent" may optionally be referred to as a "probe."

Absorbent Pads

Provided herein are absorbent pads that are impregnated with a liquid formulation, where the liquid formulation is substantially evenly distributed throughout the pad. A pad of the present disclosure is typically wettable and able to absorb the liquid formulation, retain the liquid formulation, and/or maintain a substantially even distribution of the liquid formulation during storage and during the methods described herein. In some embodiments, absorbent pads of the present disclosure, are a fibrous material that is woven or a nonwoven and that contain natural fibers, synthetic fibers, or a combination thereof. In some embodiments, a pad of the present disclosure comprises a polyester, a cellulose polymer, a polyamide, cotton, fleece, felt, a glass fiber, a filter paper, a soft wood filter, nylon, or a combination of one, two or more thereof. In some embodiments, a pad of the present disclosure comprises a polymer or a polymer blend. In some embodiments, a pad of the present disclosure comprises a polyamide, a polyester, a cellulose, or a combination of one, two or more thereof. In some embodiments, a pad of the present disclosure comprises a polyester or a polyester/cellulose blend. In some embodiments, a pad of the present disclosure comprises polyethylene terephthalate or a polyamide/polyethylene terephthalate blend.

In some embodiments, a pad of the present disclosure comprises a polyester. In some embodiments, a pad of the present disclosure is 100% polyester. The polyester can be a polycondensation product of a dicarboxylic acid with a dihydroxy alcohol. Examples of dicarboxylic acids are, but not limited to, maleic acid, fumaric acid, phthalic acid, adipic acid, and terephthalic acid. Examples of dihydric alcohols are, but not limited to, ethylene glycol, diethylene glycol, propylene glycol, and dipropylene glycol. The polyesters can be long-chain polymers composed of about 50 wt % to about 98 wt % of an ester of a terephthalic acid and one of the dihydric alcohols listed above. The polyester may optionally be crosslinked. In one embodiment, the polyester is not crosslinked. In some embodiments, the polyester is a hydrophilic polyester. Hydrophilicity can be imparted to hydrophobic polyesters by conventional means, such as treatment of the polyester with a hydrophilic composition, such as an ethoxylated polyester and a surfactant. Examples of polyesters suitable for use include VWR SPEC-WIPE® (VWR Intl, Leicestershire, UK); ANTICON® and ANTICON® MILLISEAL® (Milliken & Company, LaGrange, Ga.); VECTRA® ALPHA®, ALPHAWIPE®, ALPHASORB®, ALPHA10®, and MIRACLE WIPE® (ITW-Texwipe Company, Mahwah, N.J.); and ULTRASEAL® and VALUSEAL™ (Berkshire Corporation, Great Barrington, Mass.).

In some embodiments, a pad of the present disclosure, comprises a cellulose. A cellulose material, used in a pad of the disclosure, can be a natural cellulose, a synthetic cellulose, a modified cellulose, or a combination of two or more thereof. Examples include wood pulp cellulose, cotton cellulose, cellulose acetate, hydroxypropyl cellulose, hydroxypropylmethyl cellulose, methyl cellulose, and carboxymethyl cellulose. Other cellulose materials known in the art can be used.

In some embodiments, a pad of the present disclosure comprises a polyester/cellulose blend. In some embodiments, the polyester/cellulose blend includes about 30 wt % to about 60 wt % polyester and about 40 wt % to about 70 wt % cellulose. In some embodiments, the polyester/cellulose blend includes about 40 wt % to about 50 wt % polyester and about 50 wt % to about 60 wt % cellulose. In some embodiments, the polyester/cellulose blend includes about 45 wt % polyester and about 55 wt % cellulose. In all cases, whether polyester or a polyester/cellulose blend, the material can be either woven or non-woven. In one embodiment, a pad of the present disclosure comprises a nonwoven polyester/cellulose blend. Exemplary nonwoven materials include hydroentangled polyester/cellulose blends. Examples of commercially available polyester/cellulose blends include DURX® and MICROFIRST® (Berkshire Corporation, Great Barrington, Mass.); C1 Wiper and PROZORB® (Contec, Spartanburg, S.C.); and TECHNICLOTH® (ITW-Texwipe Company, Mahwah, N.J.).

A pad of the present disclosure, in some embodiments, has one or more properties including, but not limited to: thickness, weight, sorbency, number of fibers, number of layers and number of pads.

In some embodiments, the thickness of a pad of the present disclosure should typically be great enough to allow the pad to retain enough liquid formulation to allow the transport of components from the pad to the blot membrane. Generally, the thickness of a pad of the present disclosure is from about 0.1 mm to about 1 mm; or from about 0.2 mm to about 0.8 mm. In some embodiments, a pad of the present disclosure has a thickness from about 0.2 mm to about 1 mm. In some embodiments, a pad of the present disclosure has a thickness from about 0.2 mm to about 0.4 mm; or from about 0.2 mm to about 0.3 mm. In some embodiments, a pad of the present disclosure has a thickness from about 0.3 mm to about 0.7 mm; or from about 0.4 mm to about 0.5 mm. In some embodiments, a pad of the present disclosure has a thickness from about 0.5 mm to about 0.8 mm; or from about 0.6 mm to about 0.7 mm.

In some embodiments, sorbency is a property of a pad of the present disclosure. Sorbency (intrinsic or extrinsic) is measured by the weight gained by a pad when it is saturated with water at normal room temperature (20°-22° Celsius), where the gram weight of water absorbed by a pad of the present disclosure is assumed to be equivalent in magnitude to the mL volume of water (i.e., the density of water being 1 g/mL). The sorbency can be determined by standard methods know in the art, such as D. W. Cooper, "Understanding Wiper Absorption Capacity and Rate," A2C2 (now Controlled Environments), September 1999. Generally, the extrinsic sorbency of a pad of the present disclosure is from about 100 mL/m$^2$ to about 600 mL/m$^2$; from about 200 mL/m$^2$ to about 500 mL/m$^2$; or from about 300 mL/m$^2$ to about 400 mL/m$^2$. In some embodiments, the extrinsic sorbency of a pad of the present disclosure is from about 250 mL/m$^2$ to about 400 mL/m$^2$; or from about 250 mL/m$^2$ to about 350 mL/m$^2$. In some embodiments, the extrinsic sorbency of a pad of the present disclosure is from about 280 mL/m$^2$ to about 320 mL/m$^2$. In some embodiments, the extrinsic sorbency of a pad of the present disclosure is from about 290 mL/m$^2$ to about 310 mL/m$^2$. Generally, the intrinsic sorbency of a pad of the present disclosure is from about 3.0 mL/g to about 6 mL/g; or from about 3.5 mL/g to about 5.8 mL/g; or about 4 mL/g to about 5.5 mL/g. In some embodiments, the intrinsic sorbency a pad of the present disclosure is from about 4.5 mL/g to about 5.2 mL/g; or from about 5.0 mL/g to about 5.2 mL/g. Generally, commercially available products have specifications that identify the extrinsic sorbency and intrinsic sorbency of pads.

In some embodiments, the basis weight is a property of a pad of the present disclosure. Basis weight is the areal density, which is the weight of a pad per unit area. The basis weight can be determined by standard methods known in the art, such as the "Standard Test Method for Mass Per Unit Area (Weight) of Fabric," D3776-96 (2002) ASTM International, West Conshohocken, Pa., 1996. Generally, pads of the present disclosure have a basis weight from about 10 g/m$^2$ to about 200 g/m$^2$; or from about 30 g/m$^2$ to about 150 g/m$^2$. In some embodiments, a pad of the present disclosure has a basis weight from about 40 g/m$^2$ to about 80 g/m$^2$; from about 50 g/m$^2$ to about 70 g/m$^2$; or from about 50 g/m$^2$ to about 60 g/m$^2$. In some embodiments, a pad of the present disclosure has a basis weight from about 80 g/m$^2$ to about 140 g/m$^2$. Commercially available products have specifications that identify the basis weight of pads.

In some embodiments, fiber count is a property of a pad of the present disclosure. Methods of measuring the fiber count are known in the art, such as the Liquid Particle Count method or the Air Particle Count method. In some embodiments, a pad of the present disclosure can have at least 50,000 fibers/m$^2$, where the fibers are greater than 100 μm. In some embodiments, a pad of the present disclosure can have about 50,000 fibers/m$^2$ to about 2 million fibers/m$^2$, where the fibers are greater than 100 μm. In some embodiments, a pad of the present disclosure can have about 800,000 fibers/m$^2$ to about 1.5 million fibers/m$^2$, where the fibers are greater than 100 μm. In some embodiments, a pad of the present disclosure can have about 900,000 fibers/m$^2$ to about 1.2 million fibers/m$^2$, where the fibers are greater than 100 m. Commercially available products have specifications that identify the fiber count of pads.

In some embodiments, the number of layers in a pad is a property of a pad of the disclosure. An absorbent pad can have one or more layers. In some embodiments, a pad of the present disclosure has one layer. In some embodiments, a pad of the present disclosure has 2 to 10 layers. In some embodiments, a pad of the present disclosure has 2 to 5 layers. In some embodiments, a pad of the present disclosure has 2 layers. In some embodiments, a pad of the present disclosure has 3 layers. In some embodiments, a pad of the present disclosure has 4 layers. For multi-layer pads, the components of the pad can be same or different. In some embodiments, for example, a multi-layered pad can have 2 layers, 3 layers, or 4 layers where each pad has a nonwoven blend of 55% cellulose and 45% polyester. As another example, a multi-layered pad can have 2 layers, where one layer is a 100% polyester pad and another layer is a 55% cellulose/45% polyester blend pad. Various other combinations are envisioned.

The length and width of the absorbent pads of the disclosure are not critical and can vary. The length and width of each pad should be at least as great as the corresponding dimensions of the blot membrane that will be used with the pad. The layered matrix formed by the blot membrane and absorbent pad should be of a length and width appropriate for use in an imaging device, such as a CCD imager.

In some embodiments, a pad of the present disclosure is a hydroentangled blend of about 55 wt % cellulose and about 45 wt % polyester, and has a basis weight of about 122 g/m$^2$; a thickness of about 0.432 mm; and an extrinsic sorbency of about 385 mL/m$^2$. Such a pad is commercially available from Essentra Porous Technologies (Chicopee, Mass.) and marketed under the name C10. In some embodiments, a pad of the present disclosure is a hydroentangled 100 wt % polyester, and has a basis weight of about 68 g/m$^2$; a thickness of about 0.279 mm; an extrinsic sorbency of about 322 mL/m$^2$; and has about 93,000 fibers/m$^2$ greater than 100 m. Such a pad is commercially available from Essentra Porous Technologies (Chicopee, Mass.) and marketed under the name C3. In some embodiments, a pad of the present disclosure is a hydroentangled blend of about 55 wt % cellulose and about 45 wt % polyester, and has a basis weight of about 68 g/m$^2$; a thickness of about 0.305 mm; an extrinsic sorbency of about 311 mL/m$^2$; and has about 971,000 fibers/m$^2$ greater than 100 m. Such a pad is commercially available from Essentra Porous Technologies (Chicopee, Mass.) and marketed under the name C30. In some embodiments, a pad of the present disclosure is a hydroentangled blend of about 55 wt % cellulose and about 45 wt % polyester, and has a basis weight of about 54 g/m$^2$; a thickness of about 0.229 mm; an extrinsic sorbency of about 299 mL/m$^2$; and has about 1.1 million fibers/m$^2$ greater than 100 µm. Such a pad is commercially available from Essentra Porous Technologies (Chicopee, Mass.) and marketed under the name C30L. In some embodiments, a pad of the present disclosure is a hydroentangled 100 wt % polyester, and has a basis weight of about 109 g/m$^2$; a thickness of about 0.381 mm; and an extrinsic sorbency of about 370 mL/m$^2$. Such a pad is commercially available from Essentra Porous Technologies (Chicopee, Mass.) and marketed under the name C3H. In some embodiments, a pad of the present disclosure is a hydroentangled 100 wt % polyester, and has a basis weight of about 136 g/m$^2$; a thickness of about 0.457 mm; and an extrinsic sorbency of about 394 mL/m$^2$. Such a pad is commercially available from Essentra Porous Technologies (Chicopee, Mass.) and marketed under the name C3SH. In some embodiments, a pad of the present disclosure is a microfiber polyamide polyethylene terephthalate, and has a basis weight of about 88 g/m$^2$; and a thickness of about 0.483 mm. Such a pad is commercially available from Essentra Porous Technologies (Chicopee, Mass.) and marketed under the name MFY.

Liquid Formulations

Absorbent pads of the present disclosure are impregnated with a liquid formulation that comprises a luminescent substrate. The disclosure provides liquid formulations comprising a luminescent substrate and, optionally, one or more components such as but not limited to: oxidizing agents, stabilizing agents, buffers, enhancers, and combinations of one, two or more thereof. In some embodiments, the disclosure provides liquid formulations comprising a luminescent substrate, an oxidizing agent, and optionally one or more components selected from the group consisting of stabilizing agents, buffers, enhancers, and combinations of one, two or more thereof. In some embodiments, the disclosure provides liquid formulations comprising a luminescent substrate, a stabilizing agent, and optionally one or more components selected from the group consisting of oxidizing agents, buffers, enhancers, and combinations of one, two or more thereof. In some embodiments, the disclosure provides liquid formulations comprising a luminescent substrate, an oxidizing agent, a stabilizing agent, and optionally one or more components selected from the group consisting of buffers, enhancers, and combinations thereof. In some embodiments, the disclosure provides liquid formulations comprising a luminescent substrate, an oxidizing agent, a stabilizing agent, a buffer, and optionally an enhancer. In some embodiments, the disclosure provides liquid formulations comprising a luminescent substrate, an oxidizing agent, a stabilizing agent, a buffer, and an enhancer.

In some embodiments, absorbent pads of the disclosure are impregnated with a liquid formulation that comprises a chemiluminescent substrate. The disclosure provides liquid formulations comprising a chemiluminescent substrate and, optionally, one or more components selected from the group consisting of oxidizing agents, stabilizing agents, buffers, enhancers, and combinations of two or more thereof. In some embodiments, the disclosure provides liquid formulations comprising a chemiluminescent substrate, an oxidizing agent, and optionally one or more components selected from the group consisting of stabilizing agents, buffers, enhancers, and combinations of two or more thereof. In some embodiments, the disclosure provides liquid formulations comprising a chemiluminescent substrate, a stabilizing agent, and optionally one or more components selected from the group consisting of oxidizing agents, buffers, enhancers, and combinations thereof. In some embodiments, the disclosure provides liquid formulations comprising a chemiluminescent substrate, an oxidizing agent, a stabilizing agent, and optionally one or more components such as but not limited to: buffers, enhancers, and combinations thereof. In some embodiments, the disclosure provides liquid formulations comprising a chemiluminescent substrate, an oxidizing agent, a stabilizing agent, a buffer, and optionally an enhancer. In some embodiments, the disclosure provides liquid formulations comprising a chemiluminescent substrate, an oxidizing agent, a stabilizing agent, a buffer, and an enhancer.

In some embodiments, absorbent pads of the disclosure are impregnated with a liquid formulation that comprises a fluorescent substrate. The disclosure provides liquid formulations comprising a fluorescent substrate and, optionally, one or more components selected from the group consisting of oxidizing agents, stabilizing agents, buffers, enhancers, and combinations of two or more thereof. In some embodiments, the disclosure provides liquid formulations comprising a fluorescent substrate, an oxidizing agent, and optionally one or more components selected from the group consisting of stabilizing agents, buffers, enhancers, and combinations of two or more thereof. In some embodiments, the disclosure provides liquid formulations comprising a fluorescent substrate, a stabilizing agent, and optionally one or more components selected from the group consisting of oxidizing agents, buffers, enhancers, and combinations of two or more thereof. In some embodiments, the disclosure provides liquid formulations comprising a fluorescent substrate, an oxidizing agent, a stabilizing agent, and optionally one or more components selected from the group consisting of buffers, enhancers, and combinations thereof. In some embodiments, the disclosure provides liquid formulations comprising a fluorescent substrate, an oxidizing agent, a stabilizing agent, a buffer, and optionally an enhancer. In some embodiments, the disclosure provides liquid formulations comprising a fluorescent substrate, an oxidizing agent, a stabilizing agent, a buffer, and an enhancer.

A luminescent substrate may be known in the art or commercially available. Generally, a luminescent substrate is a substrate that can be used to detect horseradish peroxidase, alkaline phosphatase, β-galactosidase, β-glucosidase, β-glucuronidase, arylesterase, sulfatase, or other enzyme used for biological assays and detection systems.

In some embodiments, a luminescent substrate is a chemiluminescent substrate. In some embodiments, the chemiluminescent substrate can detect horseradish peroxidase, alkaline phosphatase, β-galactosidase, β-glucosidase, β-glucuronidase, arylesterase, sulfatase, or a combination of two or more thereof.

In some embodiments, the chemiluminescent substrate is resorcinol, pyrogallol, phloroglucinol, purpurogallin, aminoaryl cyclic diacylhydrazide or a salt thereof, hydroxyaryl cyclic diacylhydrazide, a pyridopyridazine derivative, 10,10'-dimethyl-9,9-biacridane, 9-benzylidene-10-methylacridane, a substituted-9-benzylidene-10-methylacridane, N-methylacridane, a substituted N-methylacridane, 9-benzylacridane, a substituted-9-benzylacridane, 9-benzyl-N-methylacridane, a substituted-9-benzyl-N-methylacridane, N-alkylacridane-9-carboxylic acid, an ester of N-alkylacridane-9-carboxylic acid, a thioester of N-alkylacridane-9-carboxylic acid, indole-3-acetic acid, an ester of indole-3-acetic acid, a thioester of indole-3-acetic acid, N-methylindole-3-acetic acid, an ester of N-methylindole-3-acetic acid, phenyl, phenyl-2-(6'-hydroxy-2-benzothiazolyl-A$^2$-thiazoline-4-carboxylate, substituted phenyl-2-(6'-hydroxy-2-benzothiazolyl-A$^2$-thiazoline-4-carboxylate, methyl 2-(6'-hydroxy-2'-benzothiazolyl)-A$^2$-thiazoline-4- carboxylate, 2-(6'-hydroxy-2'-benzothiazolyl)-A²-thiazoline acetic acid, an ester of 2-(6'-hydroxy-2'-benzothiazolyl)-A²-thiazoline acetic acid, 2-(4'-hydroxyphenyl)thiazole-4-carboxylic acid hydrazide, 2-(6'-hydroxy-2'-benzothiazolyl)thiazole-4-carboxylic acid hydrazide, substituted or unsubstituted 9-acridanecarboxylic acid hydrazide, substituted or unsubstituted N-alkyl-9-acridanecarboxylic acid hydrazide, substituted N-alkyl-9-30 acridanecarboxylic acid hydrazide, o-hydroxybenzoic acid hydrazide, o-aminobenzoic acid hydrazide, m-hydroxybenzoic acid hydrazide, 2-hydroxy-3-naphthoic acid hydrazide, 2-amino-3-naphthoic acid hydrazide, 1-hydroxy-2-anthroic acid hydrazide, D-luciferin-O-sulphate, D-luciferin-O-phosphate, a luciferin isolated from *Pholas dactlus*, the firefly *Photinus Pyralis* or *Cypridina*, and combinations of one, two or more thereof; and wherein when the compound is an aryl compound, then the aryl component is phenyl, substituted phenyl, naphthyl, substituted naphthyl, anthxyl or substituted anthryl. Such exemplary luminescent substrates are described in U.S. Pat. No. 6,602,679, the disclosure of which is incorporated by reference herein in its entirety.

In some embodiments, a chemiluminescent substrate is one or more of luminol, isoluminol, acridane, phenyl-10-methylacridane-9-carboxylate, 2,4,6-trichiorophenyl-10-methylacndane-9-carboxylate, pyrogallol, phioroglucinol, and resorcinol. In some embodiments, a chemiluminescent substrate is luminol. In some embodiments, a chemiluminescent substrate is isoluminol. Such exemplary luminescent substrates are described in U.S. Pat. No. 6,602,679, the disclosure of which is incorporated by reference herein in its entirety In some embodiments, a chemiluminescent substrate is an acridane compound or a 1,2-dioxetane. In some embodiments, a chemiluminescent substrate is:

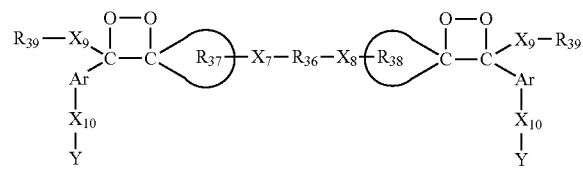

wherein each of $R_{36}$ and $R_{39}$ is an alkyl group; $R_{37}$ and $R_{38}$ are each an adamantly spirofused to the carbon atom of the dioxetane ring; Ar is a substituted phenyl which may optionally include a deuterium atom or a deuterium atom containing organic group; $X_7$, $X_8$, $X_9$, and $X_{10}$ are each oxygen; and Y is a diphosphonium group. Such exemplary luminescent substrates are described in U.S. Pat. No. 8,546,150, the disclosure of which is incorporated by reference herein in its entirety.

In some embodiments, a chemiluminescent substrate is phenyl 10-methyl($D_3$)acridan-9-carboxylate; phenyl($D_5$)10-methyl($D_3$)acridan-9-carboxylate; 2,2,2-trifluoroethyl 10-methyl($D_3$)acridan-9-carboxylate; phenyl($D_5$)10-methylacridan-9-carboxylate; 4,4'-biphenyl 10-methylacridan-9-carboxylate; [(4-methoxy($D_3$))-4-(3-hydroxy-4-chlorophenyl)]spiro[1,2-dioxetane-3,2'-adamantane]-10-methylacridan-9-carboxylate; [(4-methoxy($D_3$)-4-(3-hydroxy-4-chlorophenyl)]spiro[1,2-dioxetane-3,13-tricyclo[7.3.1.0²,⁷]tridec-2,7-ene]-10-methyl($D_3$)acridan-9-carboxylate; 4'-carboxylic acid-4-biphenyl 10-methylacridan-9-carboxylate; [4-(2-propenoic acid)]phenyl-10-methyl-9-carboxylate; bis-(1,2-ethane)10-methylacridan-9-carboxylate; bis-(1,4-phenoxy) 10 methylacridan-9-carboxylate; bis-(1,5-naphthyl) 10-methylacridan-9-carboxylate; [(4-phenoxy)-4-(3-phosphoryloxy-4-chlorophenyl)]spiro[1,2-dioxetane-3,13'-tricyclo[7.3.1.0²,⁷] tridec-2,7-ene; [4-(4-chlorophenoxy)-4-(3-phosphoryloxy-4-chlorophenyl)]spiro[1,2-dioxetane-3,13'-tricyclo[7.3.1.0²,⁷]tridec-2,7-ene; [4-(2,4,6-trichlorophenoxy)-4-(3-phosphoryloxy-4-chlorophenyl)]spiro[1,2-dioxetane-3,13'-tricyclo[7.3.1.0²,⁷]tridec-2,7-ene; [4-methoxy-4-(3-phosphoryloxy-4-cyanophenyl)]spiro[1,2 dioxetane-3,13'-tricycle[7.3.1.0²,⁷]tridec-2,7-ene; [(4-methoxy($D_3$)-4-β-phosphoryloxy-4-cyanophenyl)]spiro[1,2-dioxetane-3,2'-5-chloroadamantane]; [(4-methoxy($D_3$)-4-β-phosphoryloxy-4-cyanophenyl)]spiro[1,2-dioxetane-3,2'-5-methoxyadamantane; [(4-methoxy($D_3$)-4-(3-phosphoryloxy-4-cyanophenyl)]spiro[1,2-dioxetane-3,13'-tricycle[7.3.1.0²,⁷]tridec-2,7-ene; bis{[(4-methylenoxy)-4-(3-phosphoryloxyphenyl)]spiro[1,2-dioxetane-3,2'-adamantane]; bis-{[(4-methylenoxy)-4-(3-phosphoryloxy-4-cholorophenyl)]spiro[1,2-dioxetane-3,2'-adamantane]; bis-[(4-methoxy)-4-(3-phosphoryloxy-4-cholorophenyl)] spiro[1,2-dioxetane-3,2'-5-chloroadamantane]; bis {[(4-methoxy)-4-(3-phoryloxy-4-chlorophoryloxy-4-chloroenyl)]spiro[1,2-dioxetane-3,13'-tricyclo[7.3.1.0²,⁷]tridec-2,7-ene]; bis{(4-methoxy($D_3$)-4-β-phosphoryloxy-4-chlorophenyl)}spiro{1,2-dioxetane-3,2'-(5-oxy-adamantane)}methane; bis{(4-methoxy($D_3$)-4(3-phosphoryloxy-4-cyanophenyl)}spiro{1,2-dioxetane-3,2'-(5-oxy-adamantane)}methane; bis{(4-methoxy-4-(3-phosphoryloxyphenyl)}spiro{1,2-dioxetane-3,2'-(5-oxy-adamantane)}methane; [4-methoxy($D_3$)-4-β-β-D-galactose-4-chlorophenyl)]spiro[1,2-dioxetane-3,2'-adamantane; [(4-methoxy-4(3-β-D-galactose-4-cyanophenyl)]spiro[1,2-dioxetane-3-1,3-tricylo[7.3.1.0²,⁷]tridec-2,7-ene; [(4-methoxy($D_3$)-4-(3-β-D-glucoside-4-chlorophenyl)]spiro[1,2-dioxetane-3,2'-adamantane]; [(4-methoxy-4(3-β-D-glucoside-4-cyanophenyl)]spiro[1,2-dioxetane-3-1,3-tricylo[7.3.1.0²,⁷]tridec-2,7-ene; [(4-methoxy($D_3$)-4-(3-β-D-glucoronic acid-4-chlorophenyl)]spiro[1,2-dioxetane-3,2'-adamantane]; [(4-methoxy-4(3-β-D-glucoronic acid-4-cyanophenyl)]spiro[1,2-dioxetane-3-1,3-tricylo[7.3.1.0²,⁷] tridec-2,7-ene; [(4-methoxy($D_3$)-4-(3-acetoxy-4-chlorophenyl)]spiro[1,2-dioxetane-3,2'-adamantane]; [(4-methoxy-4(3-acetoxy-4-cyanophenyl)]spiro[1,2-dioxetane-3-1,3-tricylo[7.3.1.0²,⁷]tridec-2,7-ene; [(4-methoxy($D_3$)-4-(3-sulfate-4-chlorophenyl)]spiro[1,2-dioxetane-3,2'-adamantane]; [(4-methoxy-4(3-sulfate-4-cyanophenyl)] spiro[1,2-dioxetane-3-1,3-tricylo[7.3.1.0²,⁷]tridec-2,7-ene; or a salt of one of the foregoing. Such exemplary luminescent substrates are described in U.S. Pat. No. 8,546,150, the disclosure of which is incorporated by reference herein in its entirety.

In some embodiments, a chemiluminescent substrate is an acridane of structure (2):

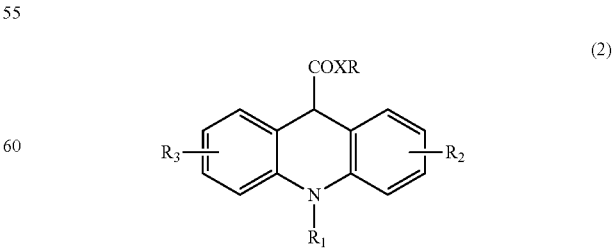

wherein X is oxygen, nitrogen or sulfur; R is methyl, deuterated methyl, phenyl, deuterated phenyl or substituted phenyl; $R_1$ is alkyl (containing up to six carbon atoms, branched or normal chain) or deuterated alkyl, aryl or deuterated aryl, arylalkyl, alkylaryl, heteroalkyl, alkylalkene, arylalkene, alkylnitrile, alkylalcohol and alkyacid; $R_2$ and $R_3$ may be alkyl or deuterated alkyl, methoxy or deuterated methoxy, Cl, Br or CN; wherein at least one of R, $R_1$, $R_2$, and $R_3$ is a deuterium atom or deuterium atom containing organic group. Such exemplary luminescent substrates are described in U.S. Pat. No. 8,546,150, the disclosure of which is incorporated by reference herein in its entirety.

In some embodiments, a chemiluminescent substrate is an acridane of structure (3):

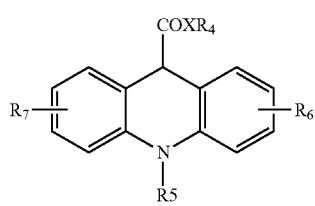

(3)

wherein X is oxygen, nitrogen or sulfur; wherein $R_4$ is an organic group to increase the solubility of substituted acridanes in an aqueous buffer; $R_5$, $R_6$ and $R_7$ are the same as $R_1$, $R_2$ and $R_3$ are in structure (2). Such exemplary luminescent substrates are described in U.S. Pat. No. 8,546,150, the disclosure of which is incorporated by reference herein in its entirety.

In some embodiments, a chemiluminescent substrate is an acridane of structure (4):

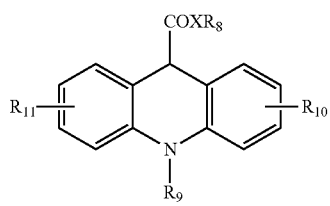

(4)

wherein $R_8$ is a substituent for increasing light output in an aqueous buffer in a chemiluminescent system, $R_9$, $R_{10}$, and $R_{11}$ are organic groups in the acridane ring as $R_1$, $R_2$ and $R_3$ are in structure (2); X is oxygen, nitrogen or sulfur. Such exemplary luminescent substrates are described in U.S. Pat. No. 8,546,150, the disclosure of which is incorporated by reference herein in its entirety.

In some embodiments, a chemiluminescent substrate is an acridane of structure (5):

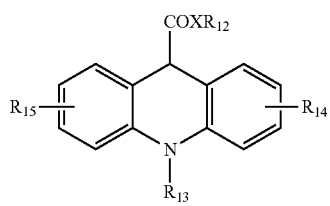

(5)

wherein $R_{12}$ is substituted 1,2-dioxetane, $R_{13}$, $R_{14}$, and $R_{15}$ are the substitution in acridane ring as $R_1$, $R_2$ and $R_3$ are in structure (2); X is oxygen, nitrogen or sulfur. Such exemplary luminescent substrates are described in U.S. Pat. No. 8,546,150, the disclosure of which is incorporated by reference herein in its entirety.

In some embodiments, a chemiluminescent substrate is an acridane of structure (6):

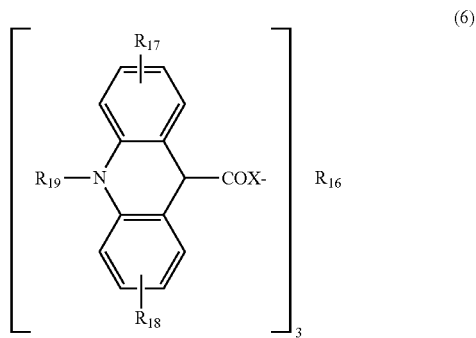

(6)

wherein $R_{16}$ is alkyl or substituted alkyl, aryl or substituted aryl, alkylaryl or substituted alkylaryl, and $R_{17}$, $R_{18}$, and $R_{19}$ are substituents in the acridane ring which may include a deuterium atom or deuterium atom containing group; X is oxygen, nitrogen or sulfur, wherein $R_{19}$ may be alkyl or deuterated alkyl, aryl or deuterated aryl, arylalkyl, alkylaryl, heteroalkyl, alkylalkene, arylalkene, alkylnitrile, alkylalcohol and alkyacid; $R_{17}$ and $R_{18}$ correspond to $R_2$ and $R_3$ above. Such exemplary luminescent substrates are described in U.S. Pat. No. 8,546,150, the disclosure of which is incorporated by reference herein in its entirety.

In some embodiments, a chemiluminescent substrate is a 1,2-dioxetane of structure (7):

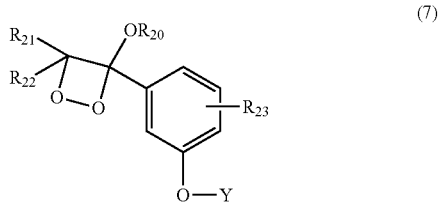

(7)

wherein Y is hydrogen, alkyl, acetate, t-butyldimethylsilyl or other protecting group, an enzyme cleavable group or an antibody cleavable group, $R_{23}$ is a substitution in the benzene ring such as hydrogen, a deuterium atom, a deuterium atom-containing group, halogen, hydroxy or substituted hydroxy, nitrile, alkyl, alkaryl, aralkyl, amino or substituted amino, nitro, aldehyde, acid, amide, aryl or substituted aryl, $R_{20}$ is an organic group having an isotopic hydrogen (deuterium atom) and is selected from the group consisting of cyclic, linear or branched, halogenated or non-halogenated alkyl, aryl, arylalkyl, alkaylaryl, heteroalkyl, heteroaryl, cycloalkyl, cycloheteroalkyl, alkyletheralkyl, alkyletheraryl, alkyl(etheralkyl)$_2$, alkyl(etheralkyl)$_3$, alkyletherhaloalkyl, alkyl(etherhaloalkyl)$_2$, alkylalkene, alkylalkyne, arylalkene, arylalkyne, alkylalcohol, alkylnitrile, alkylamine, alkylacid or the inorganic salts thereof, haloalkylalcohol, haloalkylnitrile, haloalkylamine, haloalkylacid or inorganic salts thereof, linker-fluorescent molecule, linker-antibody, linker-antigen, linker-biotin, inker-avidin, linker-protein, linker-carbohydrate or linker-lipid; or $R_{21}$ and $R_{22}$ form one of the following: (I) a cyclic, polycyclic or spiro-fused ring containing at least one carbon-carbon double bond or carbon-carbon triple bond in the ring or side chain, with or without heteroatoms; (II) a cyclic, polycyclic or a spiro-fused ring containing a substituted or unsubstituted fused aromatic ring or a substituted or unsubstituted aromatic ring attached by linker arms; (III) a cyclic, substituted or unsubstituted polycyclic alkyl group which is spiro-fused to the dioxetane ring or (IV) $R_{21}$ and $R_{22}$ are each substituted or unsubstituted branched alkyl groups or cycloalkyl groups having 3 to 8 carbon atoms and being substituted in the ring or side chain. Such exemplary luminescent substrates are described in U.S. Pat. No. 8,546,150, the disclosure of which is incorporated by reference herein in its entirety.

In some embodiments, a chemiluminescent substrate is a 1,2-dioxetane of structure (8):

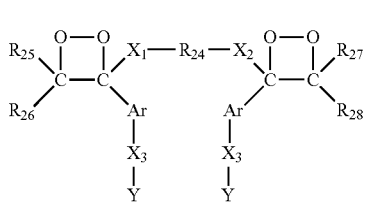

(8)

wherein $X_1$, $X_2$ and $X_3$ are each individually, sulphur or oxygen or nitrogen; $R_{24}$ is an organic group and is selected from the group consisting of cyclic, linear or branched, halogenated or non-halogenated alkyl, aryl, arylalkyl, alkylaryl, heteroalkyl, heteroaryl, cycloalkyl, cycloheteroalkyl, alkyletheralkyl, alkyletheraryl, alkyl(etheralkyl)2, alkyl(etheralkyl)3, alkyletherhaloalkyl, alkyl(etherhaloalkyl)2, alkylalkene, alkylalkyne, arylalkene, arylalkyne, alkylalcohol, alkylnitrile, alkylamine, alkylacid or the inorganic salts thereof, haloalkylalcohol, haloalkylnitrile, haloalkylamine, haloalkylacid or inorganic salts thereof, linker-fluorescent molecule, linker-antibody, linker-antigen, linker-biotin, inker-avidin, linker-protein, linker-carbohydrate or linker-lipid; $R_{25}$ and $R_{26}$ form one of the following: (I) a cyclic, polycyclic or spiro-fused ring containing at least one carbon-carbon double bond or carbon-carbon triple bond in the ring or side chain, with or without heteroatoms; (II) a cyclic, polycyclic or a spiro-fused ring containing a substituted or unsubstituted fused aromatic ring or a substituted or unsubstituted aromatic ring attached by linker arms; (III) a cyclic, substituted or unsubstituted polycyclic alkyl group which is spiro-fused to the dioxetane ring; or (IV) $R_{25}$ and $R_{26}$ are each substituted or unsubstituted branched alkyl groups or cycloalkyl groups having 3 to 8 carbon atoms and being substituted in the ring or side chain; Ar is either phenyl, substituted phenyl, naphthyl, substituted naphthyl, anthryl, substituted anthryl with or without a fluorescent group; Y is either hydrogen, alkyl, acetate, t-butyldimethylsilyl, an enzyme cleavable group or an antibody cleavable group; and $R_{24}$ is an organic group having an isotopic hydrogen(deuterium atom) and is selected from the group consisting of cyclic, linear or branched, halogenated or non-halogenated alkyl, aryl, arylalkyl, alkylaryl, heteroalkyl, heteroaryl, cycloalkyl, cycloheteroalkyl, alkyletheralkyl, alkyletheraryl, alkyl(etheralkyl)2, alkyl(etheralkyl)3, alkyletherhaloalkyl, alkyl(etherhaloalkyl)2, alkylalkene, alkylalkyne, arylalkene, arylalkyne, alkylalcohol, alkylnitrile, alkylamine, alkylacid or the inorganic salts thereof, haloalkylalcohol, haloalkylnitrile, haloalkylamine, haloalkylacid or inorganic salts thereof, linker-fluorescent molecule, linker-antibody, linker-antigen, linker-biotin, inker-avidin, linker-protein, linker-carbohydrate or linker-lipid; $R_{27}$ and $R_{28}$ are the same as $R_{25}$ and $R_{26}$, wherein individually $R_{24}$, $R_{25}$, $R_{26}$, $R_{27}$, $R_{28}$ and Ar may be a deuterium atom or deuterium atom containing organic group. Such exemplary luminescent substrates are described in U.S. Pat. No. 8,546,150, the disclosure of which is incorporated by reference herein in its entirety.

In some embodiments, a chemiluminescent substrate is a 1,2-dioxetane of structure (9):

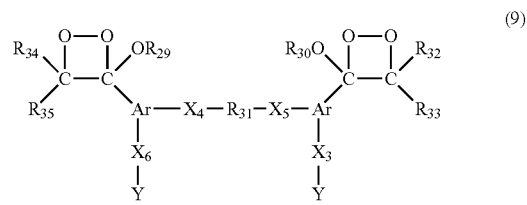

(9)

wherein $X_4$, $X_5$ and $X_6$ are each individually sulphur, oxygen or nitrogen; $R_{29}$ and $R_{30}$ is an organic group and is selected from the group consisting of cyclic, linear or branched, halogenated or non-halogenated alkyl, aryl, arylalkyl, alkylaryl, heteroalkyl, heteroaryl, cycloalkyl, cycloheteroalkyl, alkyletheralkyl, alkyletheraryl, alkyl(etheralkyl)$_2$, alkyl(etheralkyl)$_3$, alkyletherhaloalkyl, alkyl (etherhaloalkyl)$_2$, alkylalkene, alkylalkyne, arylalkene, arylalkyne, alkylalcohol, alkylnitrile, alkylamine, alkylacid or the inorganic salts thereof, haloalkylalcohol, haloalkylnitrile, haloalkylamine, haloalkylacid or inorganic salts thereof, linker-fluorescent molecule, linker-antibody, linker-antigen, linker-biotin, inker-avidin, linker-protein, linker-carbohydrate or linker-lipid; $R_{32}$ and $R_{33}$ form one of the following: (I) a cyclic, polycyclic or spiro-fused ring containing at least one carbon-carbon double bond or carbon-carbon triple bond in the ring or side chain, with or without heteroatoms; (II) a cyclic, polycyclic or a spiro-fused ring containing a substituted or unsubstituted fused aromatic ring or a substituted or unsubstituted aromatic ring attached by linker arms; (III) a cyclic, substituted or unsubstituted polycyclic alkyl group which is spiro-fused to the dioxetane ring; or (IV) $R_{32}$ and $R_{33}$ are each substituted or unsubstituted branched alkyl groups or cycloalkyl groups having 3 to 8 carbon atoms and being substituted in the ring or side chain; Ar is either phenyl, substituted phenyl, naphthyl, substituted naphthyl, anthryl, substituted anthryl with or without a fluorescent group; Y is either hydrogen, alkyl, acetate, t-butyldimethylsilyl, an enzyme cleavable group, or an antibody cleavable group; and $R_{31}$ is a aryl or alkyl linker arm; $R_{34}$ and $R_{35}$ are as described above for $R_{32}$ and $R_{33}$. Such exemplary luminescent substrates are described in U.S. Pat. No. 8,546,150, the disclosure of which is incorporated by reference herein in its entirety.

In some embodiments, a chemiluminescent substrate is a 1,2-dioxetane of structure (10):

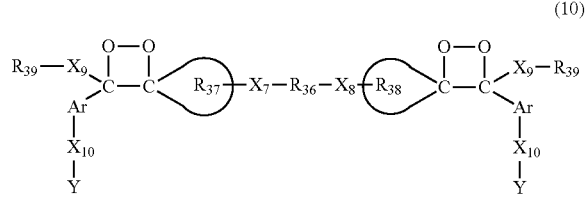

(10)

wherein $R_{36}$, $R_{37}$, $R_{38}$, $R_{39}$ and Ar may include a deuterium atom or deuterium atom containing organic group; $X_7$, $X_8$, $X_9$ and $X_{10}$ are each individually sulphur, oxygen or nitrogen, Y is either hydrogen, alkyl, acetate, t-butyldimethylsilyl, an enzyme cleavable group, or an antibody cleavable group; $R_{36}$ is an aryl or alkyl linker arm; $R_{39}$ is an organic group and is selected from the group consisting of cyclic, linear or branched, halogenated or non-halogenated alkyl, aryl, arylalkyl, alkylaryl, heteroalkyl, heteroaryl, cycloalkyl, cycloheteroalkyl, alkyletheralkyl, alkyletheraryl, alkyl(etheralkyl)2, alkyl(etheralkyl)3, alkyletherhaloalkyl, alkyl(etherhaloalkyl)2, alkylalkene, alkylalkyne, arylalkene, arylalkyne, alkylalcohol, alkylnitrile, alkylamine, alkylacid or the inorganic salts thereof, haloalkylalcohol, haloalkylnitrile, haloalkylamine, haloalkylacid or inorganic salts thereof, linker-fluorescent molecule, linker-antibody, linker-antigen, linker-biotin, inker-avidin, linker-protein, linker-carbohydrate or linker-lipid; $R_{37}$ forms one of (I) a cyclic, polycyclic or spiro-fused ring containing at least one carbon-carbon double bond or carbon-carbon triple bond in the ring or side chain, with or without heteroatoms; (II) a cyclic, polycyclic or a spiro-fused ring containing a substituted or unsubstituted fused aromatic ring or a substituted or unsubstituted aromatic ring attached by linker arms; (III) a cyclic, substituted or unsubstituted polycyclic alkyl group which is spiro-fused to the dioxetane ring; or (IV) $R_{37}$ is a substituted or unsubstituted branched alkyl groups or cycloalkyl groups having 3 to 8 carbon atoms and being substituted in the ring or side chain; $R_{38}$ is as described above for R.sub.37, wherein individually $R_{29}$, $R_{30}$, $R_{31}$, $R_{32}$, $R_{33}$, $R_{34}$, $R_{35}$ and Ar may comprise a deuterium atom or deuterium atom containing organic group. Such exemplary luminescent substrates are described in U.S. Pat. No. 8,546,150, the disclosure of which is incorporated by reference herein in its entirety.

In some embodiments, a chemiluminescent substrate is a 1,2-dioxetane of structure (11):

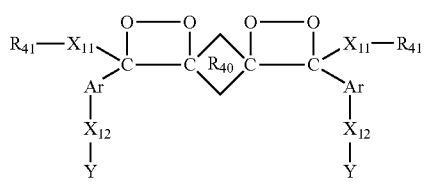

(11)

$X_{11}$ and $X_{12}$ are each, individually, sulphur, oxygen or nitrogen, Y is either hydrogen, alkyl, acetate, t-butyldimethylsilyl, an enzyme cleavable group, or an antibody cleavable group; $R_{40}$ is one of (I) a cyclic, polycyclic or spiro-fused ring containing at least one carbon-carbon double bond or carbon-carbon triple bond in the ring or side chain, with or without heteroatoms; (II) a cyclic, polycyclic or a spiro-fused ring containing a substituted or unsubstituted fused aromatic ring or a substituted or unsubstituted aromatic ring attached by linker arms; (III) a cyclic, substituted or unsubstituted polycyclic alkyl group which is spiro-fused to the dioxetane ring; or (IV) $R_{40}$ is a substituted or unsubstituted branched alkyl groups or cycloalkyl groups having 3 to 8 carbon atoms and being substituted in the ring or side chain; $R_{41}$ is an organic group and is selected from the group consisting of cyclic, linear or branched, halogenated or non-halogenated alkyl, aryl, arylalkyl, alkylaryl, heteroalkyl, heteroaryl, cycloalkyl, cycloheteroalkyl, alkyletheralkyl, alkyletheraryl, alkyl(etheralkyl)2, alkyl(etheralkyl)3, alkyletherhaloalkyl, alkyl(etherhaloalkyl)2, alkylalkene, alkylalkyne, arylalkene, arylalkyne, alkylalcohol, alkylnitrile, alkylamine, alkylacid or the inorganic salts thereof, haloalkylalcohol, haloalkylnitrile, haloalkylamine, haloalkylacid or inorganic salts thereof, linker-fluorescent molecule, linker-antibody, linker-antigen, linker-biotin, inker-avidin, linker-protein, linker-carbohydrate or linker-lipid; and Ar either phenyl, substituted phenyl, naphthyl, substituted naphthyl, anthryl, substituted anthryl with or without a fluorescent group, wherein each of $R_{40}$, $R_{41}$, and Ar may include a deuterium atom or deuterium atom containing organic group. Such exemplary luminescent substrates are described in U.S. Pat. No. 8,546,150, the disclosure of which is incorporated by reference herein in its entirety.

In some embodiments, a luminescent substrate is a fluorescent substrate. Any fluorescent substrate known in the art can be used. In some embodiments, the fluorescent substrate is a p-hydroxyphenyl compound. In some embodiments, the fluorescent substrate is 3-(4-hydroxyphenyl)propionic acid. In some embodiments, the fluorescent substrate is tyramideIR800 or 10-acetyl-3,7-dihydroxyphenoxazine. In some embodiments, the fluorescent substrate is fluorescein compound, such as fluorescein di-phosphate. In some embodiments, the fluorescent substrate is a phycobiliprotein compound, such as allophycocyanin. In some embodiments, the fluorescent substrate is a rhodamine compound, a coumarin compound, a cyanine compound (e.g., cyanine, indocarbocyanine, oxacarbocyanine, thiacarbocyanine, merocyanine), a xanthene compound, a squaraine compound, a naphthalene compound, an oxadiazole compound (e.g., pyridyloxazole, nitrobenzooxadiazole, benzooxadiazole); an anthracene compound, a pyrene compound, an oxazine compound, an acridane compound, an arylmethine compound, or a tetrapyrrole compound (e.g., porphin, phthalocyanine, bilirubin). LT01182-36-Fluorescent substrates are commercially available as QUANTABLUE™, QUANTARED™, and AMPLEX® from Thermo Fisher Scientific; AMPIFLU™ from Sigma-Aldrich; OXIRED™ from BioVision; WESTERNBRIGHT™ by Advansta.

Other exemplary substrates that can be used are made by Millipore in the LUMINATA™ series, such as CLASSICO, CRESCENDO, and FORTE.

The oxidizing agent, which can participate in the reaction of the luminescent (e.g., chemiluminescent) substrate with the enzyme or biological molecule to produce luminescence (e.g., chemiluminescence), is typically a peroxide or a compound which can produce a peroxide in situ. Exemplary oxidizing agents include hydrogen peroxide, urea hydrogen peroxide, sodium carbonate hydrogen peroxide, and a perborate salt. In some embodiments, the oxidizing agent is hydrogen peroxide. Other oxidizing agents known to those skilled in the art can be used herein. Additionally, systems which produce peroxide in situ can be used, such as a D-glucose and glucose oxidase system, as well as a cholesterol-cholesterol oxidase systems and the like.

The stabilizing agent (or stabilizer) can prevent the peroxide compound from reacting prior to addition of the enzyme or the other molecule to the formulation. Exemplary stabilizing agents include cyclodextrin, dextrin sulfate, sugars (such as glucose, sucrose and others), nonionic surfactants (such as glycerol, propylene glycol). Other stabilizers include commercially available ethylene oxide/propylene oxide adducts compounds such as polyoxyethylenesorbitan monolaurate (i.e., TWEEN® 20), polyoxyethylenesorbitan monopalmitate (i.e., TWEEN® 40), polyethylene glycol sorbitan monostearate (i.e., TWEEN® 60), polyethylene glycol sorbitan monooleate (i.e., TWEEN® 80), polyoxyethylenesorbitan trioleate (TWEEN® 85), t-octylphenoxypolyethoxyethanol (i.e., TRITON™ X-100 or reduced TRITON™ X-100), polyethylene glycol nonylphenyl ether (i.e., TRITON™ N-101 or reduced TRITON™ N-101), polyethylene glycol tert-octylphenyl ether (i.e., TRITON™ X-114 or reduced TRITON™ X-114), polyethylene glycol tert-octylphenyl ether (i.e., TRITON™ X-405 or reduced TRITON™ X-405), polyethylene glycol dodecyl ether (i.e., BRIJ® 35) and the like. TWEEN® compounds are made by Croda International. TRITON™ compounds are made by The Dow Chemical Company. Other useful stabilizers include anionic surfactants, such as lauryl sulfate, domiphen bromide, cetyltrimethyl ammonium bromide, cetyltrimethyl ammonium chloride, cetyldimethylethyl ammonium bromide (CTAB); proteins, such as bacitracin, BSA, KLH, HSA, Trypsin inhibitor; polymers such as polymeric phosphonium salts and polymeric ammonium salts. Other useful stabilizers include those compounds sold under the names DEQUEST® 2060S and coenzyme A; as well as inorganic pyrophosphates, cytidine nucleotides, ethylenediaminetetraacetic acid (EDTA), di ethylenetriaminepentaacetic acid, ethylene-bis(oxyethylenenitrilo) tetraacetic acid, and other related macromolecules as well as any other compounds capable of stabilizing the luminescent (e.g., chemiluminescent) compound in the formulation and which are known to the skilled artisan.

A liquid formulation comprising a luminescent (e.g., chemiluminescent) substrate will generally have a pH of about 5.5 to about 12.0. A buffer can be used to bring the substrate within the useful pH range. Suitable buffers include citrates, acetates, tris, borates, carbonates and phosphates, aminopropanols and the like, as well as mixtures thereof. Other exemplary buffers are ethylenediamine tetraacetic acid (EDTA), succinate, citrate, aspartic acid, glutamic acid, maleate, cacodylate, 2-(N-morpholino)-ethanesulfonic acid (MES), N-(2-acetamido)-2-aminoethanesulfonic acid (ACES), piperazine-N,N'-2-ethanesulfonic acid (PIPES), 2-(N-morpholino)-2-hydroxypropanesulfonic acid (MOPSO), N,N-bis-(hydroxyethyl)-2-aminoethanesulfonic acid (BES), 3-(N-morpholino)-propanesulfonic acid (MOPS), N-2-hydroxyethylpiperazine-N-2-ethanesulfonic acid (HEPES), 3-(N-tris-(hydroxymethyl)methylamino)-2-hydroxypropanesulfonic acid (TAPSO), 3-(N,N-bis[2-hydroxyethyl]amino)-2-hydroxypropanesulfonic acid (DIPSO), N-(2-hydroxyethyl) piperazine-N'-(2-hydroxypropanesulfonic acid) (HEPPSO), 4-(2-hydroxyethyl)-1-piperazine propanesulfonic acid (EPPS)N-[tris(hydroxymethyl)-methyl]glycine (Tricine), N,N-bis(2-hydroxyethyl)glycine (Bicine), (2-hydroxy-1,1-bis(hydroxymethyl)ethyl)amino]-1-propanesulfonic acid (TAPS), N-(1,1-dimethyl-2-hydroxyethyl)-3-amino-2-hydroxypropanesulfonic acid (AMPSO), tris(hydroxy methyl) amino-methane (Tris), and bis[2-hydroxyethyl]iminotris-[hydroxymethyl]methane (BisTris). Suitable acids or bases, as needed, can be used to adjust the pH of the buffer or buffers to bring the final pH of the formulation to about 5.5 to about 12.0.

A liquid formulation comprising a luminescent substrate can also include a luminescence enhancer (enhancer or enhancing agent). Generally, the enhancer is an organic compound which is soluble in an organic solvent or in a buffer and which enhances the luminescent reaction between the luminescent (e.g., chemiluminescent) substrate, the oxidant and the enzyme or other biological molecule. Exemplary enhancers include halogenated phenols, such as p-iodophenol, p-bromophenol, p-chlorophenol, 4-bromo-2-chlorophenol, 3,4-dichlorophenol; alkylated phenols, such as 4-methylphenol and, 4-tert-butylphenol, 3-(4-hydroxyphenyl) propionate and the like; 4-benzylphenol; 4-(2',4'-dinitrostyryl) phenol; 2,4-dichlorophenol; p-hydroxycinnamic acid; p-fluorocinnamic acid; p-nitroicinnamic acid; p-aminocinnamic acid; m-hydroxycinnamic acid; o-hydroxycinnamic acid; 4-phenoxyphenol; 4-(4-hydroxyphenoxy) phenol; p-phenylphenol; 2-chloro-4-phenylphenol; 4'-(4'-hydroxyphenyl) benzophenone; 4-(phenylazo) phenol; 4-(2'-carboxyphenylaza) phenol; 1,6-dibromonaphtho-2-ol; 1-bromonaphtho-2-ol; 2-naphthol; 6-bromonaphth-2-ol; 6-hydroxybenzothiazole; 2-amino-6-hydroxybenzothiazole; 2,6-dihydroxybenzothiazole; 2-cyano-6-hydroxybenzothiazole; dehydroluciferin; firefly luciferin; phenolindophenol; 2,6-dichlorophenolindophenol; 2,6-dichlorophenol-o-cresol; phenolindoaniline; substituted or unsubstituted N-alkylphenoxazine; substituted or unsubstituted N-alkylphenothiazine; substituted or unsubstituted N-alkylpyrimidylphenoxazine; N-alkylpyridylphenoxazine; substituted or unsubstituted 2-hydroxy-9-fluorenone; and substituted or unsubstituted 6-hydroxybenzoxazole. Other enhancers include a protected enhancer that can be cleaved by the enzyme, such as p-phenylphenol phosphate or p-iodophenol phosphate or other phenolic phosphates having other enzyme cleavable groups, as well as p-phenylene diamine and tetramethyl benzidine. Others are fluorescein, such as 5-(n-tetradecanyl) amino fluorescein and the like. Enhancers can be used alone or a combination of two or more enhancers can be used.

A liquid formulation can include a solubilizing agent to increase the solubility of both the enhancer, when used, and a luminescent (e.g., chemiluminescent) substrate in an aqueous buffer solution. When a chemiluminescent substrate and enhancer are not water soluble any suitable organic solvent such as dimethyl sulfoxide, dimethyl formamide, dioxane, tetrahydrofuran and alcohols can be used with the stabilizers such as a solubilizer.

In preparing a liquid formulation according to the disclosure, exemplary components can be used in the following amounts: (a) a luminescent (e.g., chemiluminescent) substrate can be present in an amount from about 0.1 µM to about 200 mM, or from about 1.0 µM to about 20 mM, based on the total composition; (b) an oxidant can be present in an amount from about 0.5 µM to about 250 mM, or from about 5.0 µM to about 15 mM, based on the total composition; (c) a stabilizing agent can be present in an amount from about 0.01% to about 40% by volume, or from about 0.25 to about 10% by volume, based on the total volume; and (d) a buffer can be present in an amount from about 0.1 mM to about 10 M, or from about 1.0 mM to about 2 M, based on the total volume. When used, an enhancer can be present in an amount from about 0.1 µM to about 200 mM, or from about 1.0 µM to about 20 mM, based on the total volume. A solubilizing agent, when used, can be present in an amount from about 0.1 to about 20% by volume, or from about 0.5 to about 7.5% by volume, based on the total volume. The balance of the composition is water or one of the buffers enumerated above, or mixtures thereof. Methods for making the liquid formulations described herein can be made by processes known in the art, and exemplified in U.S. Pat. No. 6,602,679, the disclosure of which is incorporated by reference herein in its entirety.

Kits

The present disclosure, in some embodiments, provides kits which include one or more of the absorbent pads described herein. The kits can optionally include other components, such as instructions for use or other materials, reagents, standards, or the like, that would be useful for the method or process that the kit is used for and/or for providing or improving the images to be obtained by a method such as a blot assays described herein.

A kit of the present disclosure, in various embodiments, comprises one or more of the various absorbent pads as described in embodiments infra and supra wherein an absorbent pad contains a fibrous material and a liquid formulation, and wherein the liquid formulation contains a luminescent substrate. A kit of the disclosure can comprise absorbent pads having a fibrous material, and a liquid formulation comprising a chemiluminescent substrate or a fluorescent substrate, including any of the exemplary fibrous materials and substrates as set forth in other sections herein.

In some embodiments, a kit of the disclosure comprising one or more absorbent pads of the disclosure, can comprise a liquid formulation further comprising one or more reagents including: an oxidizing agent, a buffer, a stabilizing agent, an enhancer, or a combination thereof.

In some embodiments, a kit of the disclosure, can further comprise a detection agent, packaged in separate container or packaging from the absorbent pads. In some embodiments, a detection agent of a kit of the disclosure comprises an antibody or a fragment thereof. Exemplary detection agents include a primary antibody or a fragment thereof bound directly to or capable of binding to a biomolecule analyte; a secondary antibody or a fragment thereof bound to or capable of binding to a primary antibody or a fragment thereof. In some embodiments, the secondary antibody or fragment thereof is attached to an enzyme or comprises an enzyme and is reactive with the substrate in the absorbent pad.

In some embodiments, the enzyme is horseradish peroxidase, alkaline phosphatase, β-galactosidase, β-glucosidase, β-glucuronidase, arylesterase, sulfatase, or a combination thereof and the substrate is a substrate for any of these enzymes.

In some embodiments, a kit includes a container that can hold one or a plurality of absorbent pads. In some embodiments, the container can hold from 1 to about 500 pads; from 1 to about 250 pads; from 1 to about 100 pads; from 1 to about 50 pads; from 1 to about 25 pads; or from 1 to about 10 pads. A container used in a kit of the disclosure provides short-term and/or long-term storage stability for absorbent pads contained therein. In some embodiments, containers of a kit provide for storage stability from about 1 month to about 5 years; about 1 month to about 3 years; from about 3 months to about 3 years; from about 6 months to about 3 years; or from about 1 year to about 3 years.

In some embodiments, absorbent pads in a kit of the disclosure are individually wrapped or packaged within a container of the kit. The packaging for the absorbent pads can be a material known in the art that will provide suitable storage stability and that will prevent degradation of the compounds in the liquid formulation. In some embodiments, the packaging is transparent. In some embodiments, the packaging is plastic or cellophane. In some embodiments, the packaging is perforated (or similarly sealed) to allow for easy opening and retrieval of the absorbent pad therein. In some embodiments, the perforation is a seam around the edge of the absorbent pad, i.e., the seam does not traverse a face of the absorbent pad that will ultimately come into fluid contact with the blot membrane.

In some embodiments, the packaging for the absorbent pad optionally serves two purposes. First, the packaging typically provides storage stability and facilitates transport and convenient storage. Second, the packaging can typically be transparent for use in a luminescent imaging device; to facilitate contact between the blot membrane and the absorbent pad; and to transfer the membrane/pad matrix to the imaging device, as described in more detail herein.

Blot Membrane-Absorbent Pad Matrix

The preparation of blot membranes is described herein, and by processes known in the art. Once the blot membrane is processed and prepared, it is brought into contact with the absorbent pads described herein. With reference to FIG. 1, a blot membrane (10) is placed on top of an absorbent pad (11) to form a layered matrix (13). The blot membrane (10) is in fluid communication with the absorbent pad (11) thereby allowing the liquid formulation impregnated in the absorbent pad (11) to flow into the blot membrane (10). As the liquid formulation flows into the blot membrane (e.g., permeates into the blot membrane; diffuses from the absorbent pad into the blot membrane), the luminescent (e.g., chemiluminescent, fluorescent) substrate comes into contact with the detection agent on the biomolecule analyte to generate a luminescent (e.g., chemiluminescent, fluorescent) signal. The skilled artisan will appreciate that in addition to the liquid formulation flowing into the blot membrane (10), it is possible that biomolecule analyte could potentially flow toward the absorbent pad (11) and that any movement between the layers is not necessarily one-directional. The layered matrix (13) can then be placed in an imaging device to detect and/or quantify the luminescent (e.g., chemiluminescent, fluorescent) signal.

As can be seen from FIG. 1, the blot membrane (10) and absorbent pad (11) are coaptively aligned to form the layered matrix (13), i.e., the edges of the blot membrane (10) in the length and width directions and the edges of the absorbent pad (11) in the length and width directions are substantially aligned. In an alternative embodiment, the absorbent pad (11) can be placed on top of the blot membrane (10).

With reference to FIG. 2, a transparent sheet protector (12) can be placed on top of the blot membrane (10). The sheet protector (12) is coaptively aligned with the blot membrane (10), which is coaptively aligned with the absorbent pad (11), thereby forming a second layered matrix (14). An advantage of the sheet protector (12) is to provide a means to assist fluid contact between the blot membrane (10) and absorbent pad (11) without disturbing the biomolecule analyte in the blot membrane (10). In some embodiments, a blot membrane roller is applied against the top of the sheet protector (12) and rolled in a back and forth motion until the blot membrane (10) is completely wetted by the liquid formulation in the absorbent pad (11) and/or until all the air bubbles are removed from between the sheet protector (12) and the blot membrane (10). Besides a roller, other means of pressure can be applied to the sheet protector (12) to assist in providing fluid contact between the blot membrane (10) and the absorbent pad (11). Thereafter, the second layered matrix (14) can be placed in an imaging device to detect the luminescent (e.g., chemiluminescent, fluorescent) signal. In an alternative embodiment, the transparent sheet protector (12) can be removed from the blot membrane (11) prior to placing the matrix in the imaging device.

With reference to FIG. 2, a second transparent sheet protector (not shown) can optionally be placed beneath the absorbent pad (11) so that the layered blot membrane/absorbent pad is flanked on both sides by a protective sheet. In some embodiments, the transparent protector sheet (12) is not present, but a second transparent sheet protector (not shown) is placed beneath the absorbent pad (11). The second transparent sheet protector can be present when the matrix is placed in the imaging device or it can be removed before the matrix is placed in the imaging device.

The thicknesses of the layers (10), (11), and (12) shown in FIGS. 1 and 2 are not to scale and are not representative of the actual thicknesses or relative thicknesses of any of the transparent sheet protector (12), blot membrane (10), or absorbent pad (11). Similarly, although the absorbent pad (11) shown in FIGS. 1 and 2 is represented as a single layer, the skilled artisan will appreciate from the present disclosure that the absorbent pad can optionally comprise a plurality of layers as described herein.

Methods of Use

The disclosure provides methods for detecting biomolecule analytes in biological samples by (a) placing the matrix (13) shown in FIG. 1 in a luminescent imaging device; and (b) detecting light emitted from the luminescent reaction, thereby detecting the biomolecule analyte. In some embodiments, the luminescent imaging device is a chemiluminescent imaging device and the luminescent reaction is a chemiluminescent reaction. In some embodiments, the luminescent imaging device is a fluorescent imaging device and the luminescent reaction is a fluorescent reaction. In some embodiments, step (b) can be measured and viewed over a period of time in order to obtain the optimum signal for identifying and quantifying the biomolecule analyte. The luminescent signal can be continually measured in the luminescent imaging device or can be measured at different time points. The period of time can be from about 1 minute to about 2 hours; or from about 1 minute to about 1 hour; or about 5 minutes to about 20 minutes.

The disclosure provides methods for detecting biomolecule analytes in biological samples by (a) placing the matrix (14) shown in FIG. 2 in a luminescent imaging device; and (b) detecting light emitted from the luminescent reaction, thereby detecting the biomolecule analyte. In some embodiments, the luminescent imaging device is a chemiluminescent imaging device and the luminescent reaction is a chemiluminescent reaction. In some embodiments, the luminescent imaging device is a fluorescent imaging device and the luminescent reaction is a fluorescent reaction. In other embodiments, the matrix (14) in FIG. 2 further comprises a second sheet protector beneath the absorbent pad.

The disclosure provides method for detecting biomolecule analytes in biological samples by the following steps: (a) separating biomolecular components of a biological sample using gel electrophoresis thereby forming a separation gel comprising separated biomolecular components, where the separated biomolecular components comprise at least one biomolecule analyte; (b) transferring the separated biomolecular components to a blot membrane; (c) contacting the blot membrane with a detection agent and allowing the detection agent to bind to the biological analyte, wherein the detection agent is reactive with a luminescent substrate; (d) contacting the blot membrane with any of the absorbent pads that are described in detail herein to react the luminescent substrate with the detection agent thereby forming a luminescent signal; and (e) detecting the luminescent signal thereby detecting the biomolecule analyte.

The disclosure provides method for detecting biomolecule analytes in biological samples by the following steps: (a) separating biomolecular components of a biological sample using gel electrophoresis thereby forming a separation gel comprising separated biomolecular components, where the separated biomolecular components comprise at least one biomolecule analyte; (b) transferring the separated biomolecular components to a blot membrane; (c) contacting the blot membrane with a detection agent and allowing the detection agent to bind to the biological analyte, wherein the detection agent is reactive with a chemiluminescent substrate; (d) contacting the blot membrane with an absorbent pad as described in detail herein to react the chemiluminescent substrate with the detection agent thereby forming a chemiluminescent signal; and (e) detecting the chemiluminescent signal thereby detecting the biomolecule analyte.

The disclosure provides method for detecting proteins of interest in biological samples by the following steps: (a) separating biomolecular components of a biological sample using gel electrophoresis thereby forming a separation gel comprising separated biomolecular components, where the separated biomolecular components comprise at least one protein of interest; (b) transferring the separated biomolecular components to a blot membrane; (c) contacting the blot membrane with a one or more antibodies linked to one or more enzymes and allowing the antibodies to bind to the protein of interest, wherein the antibodies comprises enzymes that are reactive with a chemiluminescent substrate; (d) contacting the blot membrane with an absorbent pad as described in detail herein to react the chemiluminescent substrate with the enzymes thereby forming a chemiluminescent signal; and (e) detecting the chemiluminescent signal thereby detecting the protein of interest.

The disclosure provides method for detecting biomolecule analytes in biological samples by the following steps: (a) separating biomolecular components of a biological sample using gel electrophoresis thereby forming a separation gel comprising separated biomolecular components, where the separated biomolecular components comprise at least one biomolecule analyte; (b) transferring the separated biomolecular components to a blot membrane; (c) contacting the blot membrane with a detection agent and allowing the detection agent to bind to the biological analyte, wherein the detection agent is reactive with a fluorescent substrate; (d) contacting the blot membrane with an absorbent pad as described in detail herein to react the fluorescent substrate with the detection agent thereby forming a fluorescent signal; and (e) detecting the fluorescent signal thereby detecting the biomolecule analyte.

Light emitted by the present methods can be detected by any suitable known luminescent (e.g., chemiluminescent, fluorescent) imaging device, such as a luminometer, x-ray film, high speed photographic film, a charge-coupled device (CCD) camera, or visually. Each detection means has a different spectral sensitivity. The human eye is optimally sensitive to green light, CCD cameras display maximum sensitivity to red light, X-ray films with maximum response to either UV to blue light or green light are available. Choice of the detection device will be governed by the application and considerations of cost, convenience, and whether creation of a permanent record is required. In some embodiments, the light emitted is detected with a charge-coupled device camera. CCD cameras are commercially available, e.g., through Thermo Fisher Scientific (e.g., myECL™ Imager, iBright Imaging Systems), GE Healthcare (e.g., Amersham Imager 600), Azure Biosystems (e.g., Azure c500 Western Blot Imaging System), and others.

The disclosure provides a device system that includes an absorbent pad as described herein and a luminescent imaging device, such as a chemiluminescent imaging device. The disclosure provides a device system that includes an absorbent pad as described herein and a charge-coupled device (CCD) camera. The disclosure provides a device system that includes a layered matrix (13) as shown in FIG. 1 and a luminescent imaging device, such as a chemiluminescent imaging device. The disclosure provides a device system that includes a layered matrix (13) as shown in FIG. 1 and a charge-coupled device (CCD) camera. The disclosure provides a device system that includes a layered matrix (14) as shown in FIG. 2 and a luminescent imaging device, such as a chemiluminescent imaging device. In the embodiment, the layered matrix (14) may optionally further include a second transparent sheet protector adjacent and beneath the absorbent pad (11). The disclosure provides a device system that includes a layered matrix (14) as shown in FIG. 2 and a charge-coupled device (CCD) camera. In the embodiment, the layered matrix (14) may optionally further include a second transparent sheet protector adjacent and beneath the absorbent pad (11).

EXAMPLES

The following examples are for purposes of illustration only and are not intended to limit the scope of the claims.

Example 1

A Western blot assay was performed. Proteins were separated by SDS-PAGE. The proteins were then transferred to a nitrocellulose blot membrane (hereafter "blot membrane"). Other blot membranes (e.g., polyvinylidene fluoride) can be used. Unoccupied sites on the blot membrane were blocked using a blocking buffer. The blot membrane was incubated with a primary antibody at an appropriate dilution (diluted in blocking buffer or equivalent) for 1 hour at room temperature. The incubation can alternatively be conducted overnight at a temperature of 4° C. The blot membrane was thoroughly washed in a wash buffer. The blot membrane was then incubated with an enzyme-conjugate secondary antibody at an appropriate dilution (diluted in blocking buffer or equivalent) for a minimum of 30 minutes at room temperature. The blot membrane was then washed in a buffer.

Example 2

A kit comprising absorbent pads include one or more absorbent pads and each absorbent pad can be individually wrapped in a package (e.g., a transparent protective envelope made of plastic, cellophane, or the like). One package can be removed from the kit and an absorbent pad can be removed from the package for use. The package can optionally be used as the sheet protector.

Exemplary kits of the disclosure were tested. In some example embodiments, kits of the disclosure comprised exemplary absorbent pads that were made of either an 8 cm×8 cm (mini) or 8 cm×13.5 cm (midi) sheet of 55% cellulose/45% polyester (such as, but not limited to, C30, Essentra) pre-soaked with a one-component chemiluminescent substrate (such as, but not limited to, FEMTOGLOW, Michigan Diagnostics), and placed in a heat-sealed, clear cellophane wrapping.

Testing was done by cutting open the wrapping along 3 sides to create a "flap" that could be pulled back from, and replaced once a blot to be tested was placed directly on top of the absorbent pad. Therefore, the cellophane wrapping doubled as the clear sheet protector typically used to encase Western blots prior to imaging.

Example 3

The blot membrane prepared in Example 1 was utilized in this example and is represented as (10) in FIGS. 1 and 2. The blot membrane (10) was placed on top of the absorbent pad (11), e.g., a nonwoven polyester/cellulose polymer blend, to form the layered matrix (13), as shown in FIG. 1, wherein the blot membrane (10) was in fluid communication with the absorbent pad (11). A transparent, plastic sheet protector (12) was placed on top of the blot membrane (10), as shown in FIG. 2. In addition, a transparent plastic sheet protector (not shown expressly in FIG. 2) was also placed on the bottom of the layered matrix 13. A blot membrane roller was applied against the top of the sheet protector (12), and rolled in a back and forth motion until the blot membrane (10) was completely wetted by the liquid formulation in the absorbent pad (11). The matrix (14) shown in FIG. 2 was placed in a charge-coupled device (CCD) imager for one hour.

Example 4

In the present Example, two exemplary absorbent pads of the disclosure were tested as compared to prior art methods that use liquid substrate and do not use pads. Serial dilutions of HeLa cell lysate were loaded onto SDS-PAGE gels. Following separation, proteins were transferred to nitrocellulose membranes and blocked with 5% milk in TBST for at least 1 hour at room temperature. The blots were probed with an Hsp90 alpha polyclonal antibody overnight at 4° C., followed by an HRP-conjugated secondary antibody for at least 30 minutes at room temperature.

Exemplary Materials used for the blots, the results of which are shown in FIG. 3, were as follows: 1. No Pad=Liquid substrate=one-component chemiluminescent substrate (FEMTOGLOW, Michigan Diagnostics) LT01182-48-2. Absorbent Pad 1=Microfiber polyamide (MFY, Essentra), pre-soaked with FEMTOGLOW prior to adding blot for development 3. Absorbent Pad 2=55% cellulose/45% polyester, lightweight (C30L, Essentra), pre-soaked with FEMTOGLOW prior to adding blot for development 4. Membrane=Nitrocellulose Blots were developed by either incubating in liquid substrate (depicted as "No Pad" in FIG. 3), for 5 minutes, or by placing on the indicated pre-soaked absorbent pad inside a sheet protector for 5 minutes (depicted as "Absorbent Pad 1 or 2" in FIG. 3). For the blots that were placed on the pad in the sheet protector, a roller was used to apply pressure along the length of the membrane to facilitate contact with the pre-soaked absorbent pads. All three sets of blots were imaged using a CCD Camera at various time points over the course of an hour.

Results are shown in FIG. 3. Initially, signal obtained with the liquid substrate ("No Pad"), was much more intense than that obtained with the pre-soaked absorbent pads ("Absorbent Pad 1" or "Absorbent Pad 2"). However, over time the signal initially obtained with the liquid substrate decayed, whereas signal accumulation was observed on the blots incubated with the absorbent pads. Of the two absorbent pad materials tested, greater signal accumulation and less signal decay was observed with the 55% cellulose/45% polyester absorbent pad.

Example 5

In this Example, a number of different substrates have been tested, including substrates from Michigan Diagnostics, Millipore, and Thermo Fisher Scientific. Most of the substrates were one component, but two component substrates have also been tested (results not shown). Signal was obtained with all substrates.

Some exemplary substrates tested are described here. Serial dilutions of HeLa cell lysate were loaded onto SDS-PAGE gels. Following separation, proteins were transferred to nitrocellulose membranes and blocked with 5% milk in TBST for at least 1 hour at room temperature. The blots were probed with a Rab9 monoclonal antibody overnight at 4° C., followed by an HRP-conjugated secondary antibody for at least 30 minutes at room temperature.

Figure 4:
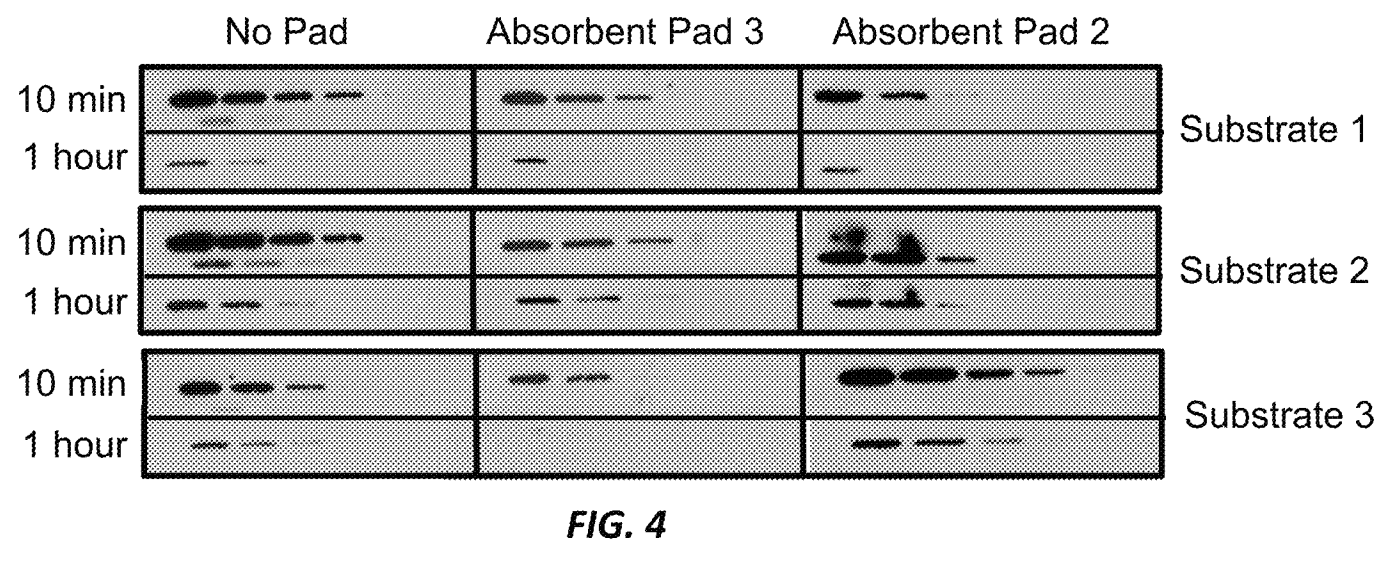

Exemplary Materials used for the blots, the results of which are shown in FIG. 4, were as follows: 1. Substrate 1=one-component chemiluminescent substrate (FEMTO-GLOW, Michigan Diagnostics) 2. Substrate 2=one-component chemiluminescent substrate (LUMINATA CRESCENDO, Millipore) 3. Substrate 3=one-component chemiluminescent substrate (CPSOC, Sigma) 4. Absorbent Pad 2=55% cellulose/45% polyester, lightweight (C30L, Essentra), pre-soaked with one of the above substrates prior to adding blot for development 5. Absorbent Pad 3=55% cellulose/45% polyester (C30, Essentra), pre-soaked with one of the above substrates prior to adding blot for development 6. Membrane=Nitrocellulose Blots were developed by either incubating in liquid substrate for 5 minutes (depicted as "No Pad" in FIG. 4), or by placing on the indicated pre-soaked absorbent pad inside a sheet protector for 5 minutes (depicted as "Absorbent Pad 1" or "Absorbent Pad 2" in FIG. 4). For the blots that were placed on the pad in the sheet protector, a roller was used to apply pressure along the length of the membrane to facilitate contact with the pre-soaked absorbent pads. All three sets of blots were imaged on X-ray film at various time points over the course of an hour. The 10-minute and 1-hour time points are shown.

Results are shown in FIG. 4. At the 10-minute time point, greater signal intensity is observed with liquid substrate 1 and liquid substrate 2, as compared to liquid substrate 3, but by 1 hour the signal remaining with liquid substrate 3 is similar to that remaining with liquid substrate 1. This suggests that the signal kinetics (including initial signal output and signal duration) of different liquid substrates can vary. The same appears to be true when the absorbent pads are pre-soaked with liquid substrates. For example, a similar signal intensity was observed at both the 10-minute and 1-hour time points when substrate 1 and substrate 2 were used to pre-soak absorbent pad 3, but a greater signal intensity was observed on absorbent pad 2 pre-soaked with substrate 2 than with substrate 1, indicating that substrate performance can vary depending on the absorbent pad. Greater sensitivity (as indicated by a greater number of bands) was observed at the 10-minute time point when absorbent pad 2 was pre-soaked with substrate 3, as compared to when it was pre-soaked with substrate 2.

Example 6

In this example, Serial dilutions of HeLa cell lysate were loaded onto SDS-PAGE gels. Following separation, proteins were transferred to nitrocellulose membranes and blocked with 5% milk in TBST for at least 1 hour at room temperature. The blots were probed with an Hsp90 alpha polyclonal antibody overnight at 4° C., followed by the indicated concentrations of HRP-conjugated secondary antibody for at least 30 minutes at room temperature.

Exemplary Materials used for the blots, the results of which are shown in FIG. 5, were as follows: 1. Absorbent Pad=55% cellulose/45% polyester (C30, Essentra), pre-soaked with a one-component chemiluminescent substrate (FEMTOGLOW, Michigan Diagnostics) substrate prior to adding blot for development 2. No pad=Liquid substrate=two-component chemiluminescent substrate (SUPERSIGNAL WEST DURA, Thermo Fisher Scientific) 3. Membrane=Nitrocellulose.

Blots were developed by either incubating in liquid substrate (No Pad) for 5 minutes, or by placing on the indicated pre-soaked absorbent pad inside a sheet protector for 5 minutes. For the blots that were placed on the pad in the sheet protector, a roller was used to apply pressure along the length of the membrane to facilitate contact with the pre-soaked absorbent pads. All three sets of blots were imaged using a CCD Camera at various time points over the course of an hour.

The results are shown in FIG. 5. A similar level of signal intensity was observed on the blots developed using the pre-soaked absorbent pad that were probed and a higher concentration (80 ng/ml) of HRP-conjugated secondary antibody, and those developed with liquid substrate and a lower concentration (16 ng/ml) of HRP-conjugated secondary antibody. Blots developed using liquid substrate and a higher concentration (80 ng/ml) of HRP-conjugated secondary antibody displayed initial signal saturation and rapid signal burnout, as indicated by the "ghost" bands at the 30-minute and 45-minute time points. These data suggest that when high concentrations of HRP-conjugated secondary antibody is used, usable signal can be obtained using the absorbent substrate pads, which might not be obtainable when incubating blots directly in liquid substrate.

Typically, when high concentrations of HRP are used with liquid substrates, the signal will burn out quite rapidly (as shown in FIG. 5, middle panel), resulting in an absence of a band where signal was once present (also sometimes referred to as a "ghost" band). Depending on how quickly the signal burns out, the result may be difficult to capture or image. The present inventors have surprisingly found that when high concentrations of HRP are used with the substrate pads (concentrations that are high enough to result in signal burn out with commonly used liquid substrates), due to the slower signal accumulation, the signal does not burn out as rapidly and images are easier to obtain before the signal has a chance to burn out. The present compositions and methods allow for a longer detection time period and as a longer imaging time period.

All publications, including but not limited to patents and patent applications, cited in this specification are herein incorporated by reference as if each individual publication were specifically and individually indicated to be incorporated by reference herein as though fully set forth. It is to be understood that the present disclosure covers all combinations of particular groups described herein above. The application of which this description and claims forms part can be used as a basis for priority in respect of any subsequent application. The claims of such subsequent application may be directed to any feature or combination of features described herein. They may take the form of product, composition, process, or use claims and may include, by way of example and without limitation, the claims described herein.

What is claimed is:

1. A composition comprising:
   a) an absorbent pad comprising (a) a fibrous material and (b) a liquid formulation which comprises a chemiluminescent substrate; wherein the pad: (i) has a thickness from 0.2 mm to 3 mm; (ii) has an extrinsic absorbency from 150 mL/m$^2$ to 500 mL/m$^2$; and (iii) is impregnated with the liquid formulation, wherein the fibrous material comprises a polyester/cellulose polymer blend, a hydroentangled polyester/cellulose blend, nylon, or a polyamide, and b) a blot membrane in fluid contact with the absorbent pad, wherein the blot membrane comprises a biomolecule analyte bound to a detection agent, wherein the detection agent is reactive with the chemiluminescent substrate on the pad.

2. The composition of claim 1, wherein the detection agent comprises an enzyme reactive with the chemiluminescent substrate.

3. The composition of claim 1, wherein the absorbent pad has a basis weight from 25 g/m² to 100 g/m².

4. The composition of claim 3, wherein the absorbent pad has a basis weight from 50 g/m² to 70 g/m².

5. The composition of claim 1, wherein the absorbent pad has: (i) the thickness of the pad is from 0.2 mm to 1 mm; and (ii) the extrinsic absorbency of the pad is from 250 mL/m² to 400 mL/m².

6. The composition of claim 5, wherein the thickness of the pad is from 0.3 mm to 0.7 mm.

7. The composition of claim 1, wherein the polyester/cellulose polymer blend comprises 40 wt % to 50 wt % polyester and 50 wt % to 60 wt % cellulose.

8. The composition of claim 1, wherein the polyester/cellulose polymer blend comprises 45 wt % polyester and 55 wt % cellulose.

9. The composition of claim 1, wherein the chemiluminescent substrate is a substrate for horseradish peroxidase, alkaline phosphatase, β-galactosidase, β-glucosidase, β-glucuronidase, arylesterase, sulfatase, or a combination of one or more thereof.

10. The composition of claim 1, wherein the liquid formulation further comprises an oxidizing agent, a buffer, a stabilizing agent, an enhancer, or a combination of one or more thereof.

11. The composition of claim 10, wherein the oxidizing agent is a peroxide compound, a compound that produces a peroxide in situ, hydrogen peroxide, urea hydrogen peroxide, sodium carbonate hydrogen peroxide, a perborate salt, or a combination of one or more thereof.

12. The composition of claim 10, wherein the stabilizing agent is cyclodextrin, dextrin, a sulfate, a sugar, a nonionic surfactant, an anionic surfactant, an ethylene oxide/propylene oxide adduct, polyoxyethylenesorbitan monolaurate, polyoxyethylenesorbitan monopalmitate, polyethylene glycol sorbitan monostearate, polyethylene glycol sorbitan monooleate, polyoxyethylenesorbitan trioleate, t-octylphenoxypolyethoxyethanol, polyethylene glycol nonylphenyl ether, polyethylene glycol tert-octylphenyl ether, polyethylene glycol tert-octylphenyl ether, polyethylene glycol dodecyl ether, or a combination of one or more thereof.

13. The composition of claim 10, wherein the buffer is ethylenediamine tetraacetic acid, succinate, citrate, aspartic acid, glutamic acid, maleate, cacodylate, 2-(N-morpholino)-ethanesulfonic acid, N-(2-acetamido)-2-aminoethanesulfonic acid, piperazine-N,N'-2-ethanesulfonic acid, 2-(N-morpholino)-2-hydroxy-propanesulfonic acid, N,N-bis-(hydroxyethyl)-2-aminoethanesulfonic acid, 3-(N-morpholino)-propanesulfonic acid, N-2-hydroxyethyl-piperazine-N-2-ethanesulfonic acid, 3-(N-tris-(hydroxymethyl)methylamino)-2-hydroxypropanesulfonic acid, 3-(N,N-bis[2-hydroxyethyl]amino)-2-hydroxypropanesulfonic acid, N-(2-hydroxyethyl)piperazine-N'-(2-hydroxypropanesulfonic acid), 4-(2-hydroxyethyl)-1-piperazine propanesulfonic acid, N-[tris(hydroxymethyl)-methyl] glycine, N,N-bis(2-hydroxyethyl)glycine, (2-hydroxy-1,1-bis(hydroxymethyl)ethyl)amino]-1-propanesulfonic acid, N-(1,1-dimethyl-2-hydroxyethyl)-3-amino-2-hydroxypropanesulfonic acid, tris(hydroxy methyl)amino-methane, and bis[2-hydroxyethyl]iminotris-[hydroxymethyl]methane, or a combination of one or more thereof.

14. The composition of claim 10, wherein the enhancer is a halogenated phenol; an alkylated phenol; 4-benzylphenol; 4-(2',4'-dinitrostyryl) phenol; 2,4-dichlorophenol; p-hydroxycinnamic acid; p-fluorocinnamic acid; p-nitrocinnamic acid; p-aminocinnamic acid; m-hydroxycinnamic acid; o-hydroxycinnamic acid; 4-phenoxyphenol; 4-(4-hydroxyphenoxy) phenol; p-phenylphenol; 2-chloro-4-phenylphenol; 4'-(4'-hydroxyphenyl) benzophenone; 4-(phenylazo) phenol; 4-(2'-carboxyphenylaza) phenol; 1,6-dibromonaphtho-2-ol; 1-bromonaphtho-2-ol; 2-naphthol; 6-bromonaphth-2-ol; 6-hydroxybenzothiazole; 2-amino-6-hydroxybenzothiazole; 2,6-dihydroxybenzothiazole; 2-cyano-6-hydroxybenzothiazole; dehydroluciferin; firefly luciferin; phenolindophenol; 2,6-dichlorophenolindophenol; 2,6-dichlorophenol-o-cresol; phenolindoaniline; a substituted or unsubstituted N-alkylphenoxazine; a substituted or unsubstituted N-alkylphenothiazine; a substituted or unsubstituted N-alkylpyrimidylphenoxazine; N-alkylpyridylphenoxazine; a substituted or unsubstituted 2-hydroxy-9-fluorenone; a substituted or unsubstituted 6-hydroxybenzoxazole, or a combination of one or more thereof.

15. The composition of claim 1, wherein the chemiluminescent substrate is luminol, isoluminol, acridane, phenyl-10-methylacridane-9-carboxylate, 2,4,6-trichlorophenyl-10-methylacndane-9-carboxylate, pyrogallol, phloroglucinol, resorcinol, or a combination thereof.

16. A device system comprising: 1) a composition of claim 1; and 2) an imaging device.

17. A method for detecting a biomolecule analyte in a biological sample comprising:
(a) separating biomolecular components of a biological sample using gel electrophoresis thereby forming a separation gel comprising separated biomolecular components, wherein the separated biomolecular components comprise a biomolecule analyte;
(b) transferring the separated biomolecular components to a blot membrane;
(c) contacting the blot membrane with a detection agent and allowing the detection agent to bind to the biological analyte, wherein the detection agent is reactive with a luminescent substrate;
(d) contacting the blot membrane with an absorbent pad to provide the composition of claim 1, wherein the luminescent substrate reacts with the detection agent thereby forming a luminescent signal; and
(e) detecting the luminescent signal thereby detecting the biomolecule analyte.

* * * * *